(12) United States Patent
Lombardi et al.

(10) Patent No.: US 9,414,915 B2
(45) Date of Patent: Aug. 16, 2016

(54) STENT VALVE, DELIVERY APPARATUS AND METHOD THEREFOR

(75) Inventors: Fabien Lombardi, Prilly (CH); Jacques Essinger, St-Prex (CH); Stephane Delaloye, Bulach (CH); Jean-Luc Hefti, Cheseaux-Noreaz (CH); Luc Mantanus, Lausanne (CH); Youssef Biadillah, Lausanne (CH)

(73) Assignee: Symetis SA, Ecublens VD (CH)

( * ) Notice: Subject to any disclaimer, the term of this patent is extended or adjusted under 35 U.S.C. 154(b) by 190 days.

(21) Appl. No.: 13/825,219

(22) PCT Filed: Sep. 26, 2011

(86) PCT No.: PCT/EP2011/066677
§ 371 (c)(1),
(2), (4) Date: Jul. 2, 2013

(87) PCT Pub. No.: WO2012/038550
PCT Pub. Date: Mar. 29, 2012

(65) Prior Publication Data
US 2013/0274870 A1 Oct. 17, 2013

Related U.S. Application Data

(60) Provisional application No. 61/386,393, filed on Sep. 24, 2010, provisional application No. 61/431,710, filed on Jan. 11, 2011.

(30) Foreign Application Priority Data

May 15, 2011 (EP) .................................... 11004013
May 16, 2011 (EP) .................................... 11166201
Jul. 26, 2011 (EP) .................................... 11006142
Sep. 12, 2011 (WO) ................. PCT/EP2011/065744

(51) Int. Cl.
*A61F 2/24* (2006.01)
*A61F 2/95* (2013.01)

(52) U.S. Cl.
CPC ............. *A61F 2/2436* (2013.01); *A61F 2/2418* (2013.01); *A61F 2/2427* (2013.01); *A61F 2002/9505* (2013.01); *A61F 2002/9517* (2013.01); *A61F 2230/0054* (2013.01)

(58) Field of Classification Search
CPC ....... A61F 2/95; A61F 2/2418; A61F 2/2436; A61F 2/2439; A61F 2/2433; A61F 2/2427; A61F 2002/9505; A61F 2002/9517; A61F 2002/9528; A61F 2002/9534; A61F 2/24; A61F 2/243; A61F 2/962; A61B 17/3415
USPC ................... 623/2.11, 1.36, 2.36, 2.37, 1.11; 606/151
See application file for complete search history.

(56) References Cited

U.S. PATENT DOCUMENTS 5,163,955 A  11/1992  Love et al.
5,571,174 A  11/1996  Love et al.
(Continued)

FOREIGN PATENT DOCUMENTS

DE  202010007592 U1  10/2010
EP  2 033 593 A1  3/2009
(Continued)

OTHER PUBLICATIONS

International Search Report for International Application No. PCT/EP2011/066677, date of mailing Feb. 17, 2012.
(Continued)

*Primary Examiner* — David C Eastwood
*Assistant Examiner* — Mikail Mannan
(74) *Attorney, Agent, or Firm* — Cooley LLP

(57) ABSTRACT

A delivery catheter (12) for a stent valve (10), the delivery catheter having a distal portion (14) insertable into an anatomy, the distal portion comprising an accommodation region (18) for accommodating a stent-valve for delivery into the anatomy, the delivery catheter further comprising at least one sheath (20; 22) that is translatable between a closed position for at least partly closing the accommodation region and an open position for at least partly opening the accommodation region.

11 Claims, 14 Drawing Sheets

(56) References Cited

U.S. PATENT DOCUMENTS

| | | | |
|---|---|---|---|
| 5,653,749 A | | 8/1997 | Love et al. |
| 5,807,241 A | | 9/1998 | Heimberger |
| 5,989,280 A | * | 11/1999 | Euteneuer et al. ............. 623/1.1 |
| 7,329,278 B2 | * | 2/2008 | Seguin et al. .................. 623/2.1 |
| 2002/0032481 A1 | | 3/2002 | Gabbay |
| 2002/0177894 A1 | | 11/2002 | Acosta et al. |
| 2003/0212447 A1 | | 11/2003 | Euteneuer et al. |
| 2004/0260389 A1 | | 12/2004 | Case et al. |
| 2005/0113910 A1 | | 5/2005 | Paniagua et al. |
| 2005/0182483 A1 | | 8/2005 | Osborne et al. |
| 2006/0025844 A1 | | 2/2006 | Majercak et al. |
| 2006/0259136 A1 | | 11/2006 | Nguyen et al. |
| 2006/0259137 A1 | | 11/2006 | Artof et al. |
| 2006/0282157 A1 | | 12/2006 | Hill et al. |
| 2007/0233222 A1 | * | 10/2007 | Roeder et al. ................ 623/1.11 |
| 2008/0071361 A1 | * | 3/2008 | Tuval et al. ................... 623/2.1 |
| 2009/0099554 A1 | | 4/2009 | Forster et al. |
| 2010/0082094 A1 | | 4/2010 | Quadri et al. |
| 2010/0100167 A1 | * | 4/2010 | Bortlein et al. .............. 623/1.11 |
| 2010/0168834 A1 | | 7/2010 | Ryan et al. |
| 2010/0185277 A1 | | 7/2010 | Braido et al. |
| 2011/0295363 A1 | | 12/2011 | Girard et al. |
| 2013/0274870 A1 | | 10/2013 | Lombardi et al. |
| 2014/0200649 A1 | | 7/2014 | Essinger et al. |

FOREIGN PATENT DOCUMENTS

| | | | |
|---|---|---|---|
| EP | 2033593 A1 | | 11/2009 |
| EP | 2474287 A1 | | 11/2012 |
| JP | 2010-528761 A | | 8/2010 |
| WO | 9415549 A1 | | 7/1994 |
| WO | 00/00107 A1 | | 1/2000 |
| WO | 0205885 A2 | | 1/2002 |
| WO | 2007005799 A1 | | 1/2007 |
| WO | WO 2007/071436 A2 | | 6/2007 |
| WO | 2008150529 | | 11/2008 |
| WO | 2009002548 | * | 12/2008 |
| WO | 2009002548 A1 | | 12/2008 |
| WO | WO 2009/053497 | | 4/2009 |
| WO | WO 2009/053497 A1 | | 4/2009 |
| WO | 2009091509 A1 | | 7/2009 |
| WO | 2009091509 | * | 7/2009 |
| WO | WO 2009/091509 A1 | | 7/2009 |
| WO | 2009149462 A2 | | 12/2009 |
| WO | 2010045297 A2 | | 4/2010 |
| WO | WO 2010/045297 A2 | | 4/2010 |
| WO | 2011051043 A1 | | 5/2011 |
| WO | WO 2011/051043 | | 5/2011 |
| WO | 2012032187 A1 | | 3/2012 |
| WO | 2012038550 A1 | | 3/2012 |
| WO | 2012/095455 A3 | | 7/2012 |

OTHER PUBLICATIONS

Written Opinion, mailed Feb. 17, 2012, for International Application No. PCT/EP2011/066677.
International Preliminary Report on Patentability, mailed Apr. 4, 2013, for International Application No. PCT/EP2011/066677.
International Search Report and Written Opinion, mailed Feb. 17, 2012, for International Application No. PCT/EP2011/065744.
International Preliminary Report on Patentability, mailed Mar. 21, 2013, for International Application No. PCT/EP2011/065744.

* cited by examiner

# STENT VALVE, DELIVERY APPARATUS AND METHOD THEREFOR

CROSS-REFERENCE TO RELATED APPLICATIONS

The present application is a 35 U.S.C. §371 national stage entry of PCT/EP2011/066677, which has an international filing date of Sep. 26, 2011 which claims priority to U.S. patent application Ser. Nos. 61/386,393, filed Sep. 24, 2010 and 61/431,710, filed Jan. 11, 2011; European Patent Application Nos. 11004013.6, filed May 15, 2011; 11166201.1 filed May 16, 2011; 11006142.1 filed Jul. 26, 2011 and International Application No. PCT/EP2011/065744 filed Sep. 12, 2011, the disclosures of which are incorporated herein by reference in their entireties.

Non-limiting aspects of the present invention relate to transcatheter implantation of prosthetic stent-valves within the anatomy, to methods of production, and to methods and apparatus for delivering a stent-valve for implantation at a desired implantation site. In some non-limiting aspects, the invention is directed to cardiac stent-valves and/or to delivery to the heart. Additionally or alternatively, some non-limiting aspects relate to stent-valves and their delivery via a transvascular access route.

Traditional approaches for aortic valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to reduce invasiveness by using a transcatheter procedure, namely by delivering and implanting a prosthetic valve via a catheter inserted through a smaller skin incision, using either a transvascular route or a transapical route to the valve implantation site. The prosthetic valve is referred to as a stent-valve or a valved-stent.

While less invasive and arguably less complicated, transcatheter heart valve replacement devices and procedures still face various difficulties. One issue is the unpredictability of the anatomical condition of the aortic valve, for example in the presence of severe calcification. Achieving controllable, consistent deployment and anchoring of a stent-valve in such variable conditions, with access only via a remote catheter, is a challenge. An incorrectly positioned valve may fail to function well, or may damage delicate heart tissue (which may result in the patient having to be fitted with a pacemaker), or may result in leakage of blood at the interface between the stent-valve and the native tissue. A further issue for transvascular delivery is difficulty of navigating, along a tortuous and often stenosed vasculature, a delivery catheter large enough to accommodate a stent-valve for implantation. The distal end of the delivery catheter is typically in the range of 6-8 mm in diameter (18-24 French) to accommodate the stent-valve. The design of a delivery catheter has to address requirements for (i) atraumatic introduction, navigation and later withdrawal through the vasculature, and (ii) support, for example, for applying force along the length of the catheter from the proximal end, to traverse the existing valve, and manipulate the distal end to unsheath and deploy the stent-valve. These requirements often conflict, leading to compromises in design. For example, softness and flexibility of the catheter are desired for autraumaticity and ease of navigation, but reduce the ability of the catheter to provide support for force applied from the proximal end remotely to the distal end.

Additional complications relate to the small size desired for the delivery catheter, without affecting the reliability, accuracy or controllability of the deployment of the stent-valve, and ability to withdraw the catheter following deployment of a stent, for example, through a tightly-fitting introducer.

One particular type of stent-valve having a geometry promising for self-alignment and self-location even in a severely calcified native valve, is described in co-owned WO-A-2009/053497 and WO-A-2011/051043. The stent component comprises a conical lower anchoring crown defining an inflow end, a conical upper anchoring crown sloping outwardly in an opposite direction to the lower crown towards the outflow end, and stabilization arches at the outflow end. As described, the stabilization arches are deployed first for aligning the stent-valve, followed by deployment of the upper crown and finally deployment of the lower crown. A transapical delivery device is described that is easy and intuitive to use for deploying the stent-valve according to the above sequence. It may be desirable to refine the stent-valve and/or the delivery device for transvascular use.

A further issue is that it is sometimes necessary to rotate the stent about the delivery axis, such that the stent has a certain rotational alignment with regard to the native anatomy. Certain previously described designs of stent rely on correct rotational alignment between the native anatomy and the stent, in order to locate/function correctly. Other previously shown designs of stent include apertures or clearances that, when aligned properly with respect to local anatomy, permit the entrance to each coronary artery to be kept relatively clear. This benefits blood flow to the coronary arteries and/or permits later treatment of the coronary arteries by allowing access for implanting coronary stents, should this be desired for the patient in a subsequent treatment.

In devices previously described, rotation is achieved by applying a torsional force to the catheter from the proximal handle end. Ideally, the distal end should rotate at a constant rate in response to torsional force. While rotation is not generally a problem with a short catheter in a relatively straight run from the handle to the stent-carrying end (e.g. transapical), it is much more problematic with a long catheter extending on a relatively twisting and/or substantially bent path (e.g. transvascular). The friction against the arterial walls obstructs free rotation, distributing the torsion to the artery itself. As the handle-end is turned, the distal end tends to remain fixed. The torsional energy tends to build-up along the length of the catheter until the handle has been turned sufficiently that the total energy exceeds frictional resistance, whereupon the distal end springs free, and rotates through a large angle. This makes rotation adjustment relatively coarse, with it being extremely difficult to achieve fine adjustment. Thus, there is a need for a stent delivery system that enables easy rotation and flexibility when delivering a stent through a longer or curving route.

The present invention has been devised bearing all of the aforementioned issues in mind. It may be desirable (although not essential) to address and/or mitigate at least one of the foregoing issues.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments according to the present disclosure. Moreover, the description herein of any disadvantages associated with the described products,` methods, and/or apparatus, is not intended to limit the disclosure. Indeed, aspects of the disclosed embodiments may include certain features of the described products, methods, and/or apparatus without suffering from their described disadvantages.

Broadly speaking, one aspect of the present invention provides a delivery catheter for transvascular delivery of a stent-valve to an implantation site. The delivery catheter may be defined independently of the stent-valve or as part of a system in combination with a stent-valve. The invention may further comprise any one or a combination of two of more of the following features, which are all optional:

(a) The delivery catheter may have a distal portion for insertion into the anatomy, and a proximal portion, a stent-valve accommodation region at the distal portion for accommodating the stent-valve in the compressed condition for delivery, and a stem portion extending from the accommodation region towards the proximal portion (e.g., to a control handle at the proximal portion). Where defined, the stent-valve may be radially compressible to a compressed state for delivery, and radially expandable to a functional state. The stent-valve may comprise a plurality of valve leaflets, and a stent component for supporting and/or housing the valve leaflets. The stent component may be self-expanding from the compressed state, or the stent component may be non-self-expanding (in which case the delivery catheter may comprise a device for applying an expansion force to cause or force expansion).

(b) The delivery catheter may comprise may comprise a first sheath for covering a first portion of the accommodation region and/or stent-valve to constrain a first portion of the stent-valve compressed, and a second sheath for covering a second portion of the accommodation region and/or the stent-valve to constrain a second portion of the stent-valve compressed.

The second sheath may be translatable in a proximal direction to uncover the second portion. The first sheath may be translatable in a distal direction to uncover the first portion. Use of such sheaths moving in opposite directions can reduce the total distal extension of the catheter when the sheaths are open (e.g., compared to a catheter employing a single distally-moving sheath).

The first and second sheaths may be independently translatable.

The stem may have a smaller outer diameter than the first sheath and/or the second sheath.

The delivery catheter may further comprise a stent holder at the accommodation region for retaining the stent-valve in a predetermined axial position during deployment. The stent-holder may restrain the stent-valve against substantial axial movement (for example in both the distal and proximal directions). The stent holder may have a profile that mates with a portion of the stent component. For example, the mating may be such as to permit self-detachment of the stent component from the stent holder when the portion of the stent component mating with the stent holder is ultimately allowed to expand by removal of a respective sheath. In some embodiments, the stent holder is positioned towards a distal end of the accommodation region and/or is configured to mate with a distal end portion and/or inflow end portion of the stent component. Optionally, the stent holder may be at least partly overlapped by the first sheath. Optionally, the stent holder may not be overlapped by the second sheath.

The second sheath may be longer than the first sheath. Such an arrangement can reduce even further distal extension of the delivery catheter when translating the sheaths to deploy the stent-valve. The ratio of the length of second sheath divided by the length of the first sheath may, for example, be at least 1.1, or at least 1.5, or at least 2, or at least 2.5, or at least 3, or at least 3.5, or at least 4, or at least 4.5, or at least 5.

The first and second sheaths may be configured such that there is no overlap of the ends of the sheaths with each other. Avoiding an overlap can avoid excess diameter of the distal portion that might otherwise be caused by the sheath walls overlapping each other. The first and second sheaths may have substantially the same internal and/or external diameter as each other.

In some embodiments, the first and second sheaths may, in one configuration, meet substantially end to end. The delivery catheter may be used, when containing the stent-valve ready for introduction into a patient, such that the sheaths meet substantially end to end, thereby covering the length of stent-valve substantially entirely.

Alternatively, whether or not the sheaths are capable of being positioned to meet end to end, in use when containing the stent-valve ready for introduction into a patient, the sheath ends may be spaced apart from each other such that a portion of the stent-valve is not covered by either sheath. The spacing between the sheaths may, for example, be at least 1 mm, or at least 2 mm, or at least 3 mm, or at least 4 mm, or at least 5 mm, or at least 6 mm. Additionally or alternatively, the spacing may be less than 10 mm, or less than 9 mm, or less than 8 mm, or less than 7 mm, or less than 6 mm, or less than 5 mm. In one form, the spacing is between about 4 mm and about 6 mm. The spacing may correspond (e.g. approximately) to a region of the stent-valve in which inner and outer skirts overlap, and/or may reduce stress within the stent-valve in the region of the spacing.

At the accommodation region the stent-valve may be orientated with the inflow end of the stent-valve distal of the outflow end of the stent-valve.

The catheter may further comprise an interface member, having any of the associated features described hereinafter.

(c) The delivery catheter may comprise at least one sheath that is translatable from a restraining position for restraining at least a portion of the stent-valve compressed at the accommodation region, to an open position in which the respective portion of the stent-valve is uncovered for deployment from the accommodation region; and an interface member that is deployable to provide a guide surface for aiding withdrawal of the delivery catheter from the anatomy after the stent-valve has been deployed. Optionally, the catheter may be withdrawable with the interface member in a deployed state. Optionally the interface member may be retained captive on the delivery catheter, for example, at the accommodation region.

The interface member can provide significant performance advantages. In some embodiments, the distal portion of the delivery catheter may include one or more abrupt surfaces or edges that are exposed when the at least one sheath is translated open. The abrupt surfaces/edges may, for example, obstruct removal of the catheter through a tightly fitting introducer if the at least one sheath remains open. Closing the at least one sheath may be problematic if the open end an open end of the sheath initially relies on the presence of the compressed stent-valve for concentric relation with another part of the delivery catheter (e.g. concentricity of opposed first and second sheaths).

In some embodiments, the interface member may provide a guide surface for cooperating with an exposed abrupt edge of a stent holder or other component of the distal portion that is exposed when the at least one sheath is open, the guide surface defining a less-abrupt and/or a more streamlined exposed profile if the sheath remains open. The more streamlined profile can permit the distal portion of the delivery catheter to be withdrawn without substantial obstruction, even into and through a tightly fitting introducer.

Additionally or alternatively, in some embodiments, the guide surface of the interface member may serve to:
(i) at least partly cover, and/or define a profile accommodating, the edge of the sheath at its open end, and/or
(ii) centre the open end of the sheath with respect to an axis of the catheter.

Such a function may permit easier closing of the sheath if desired.

In some embodiments, the delivery catheter may comprise first and second sheaths, at least one of which is translatable as aforesaid. The other sheath may also be translatable or it may be substantially fixed. The sheaths may have respective open ends that generally face one another when the (or each) sheath is in the closed position (whether or not the sheaths contact each other end to end).

In some embodiments, the interface member may be deployable to:
(i) provide an interface at or between the generally facing open ends, and/or
(ii) align the open ends of the sheaths to be substantially in register with each other and/or centred with respect to the catheter axis, and/or (iii) define a bridge and/or a smooth profile between the facing open ends of the sheaths.

Whatever the function of the interface member, in some embodiments, the interface member may be translatable along the catheter axis from a non-deployed condition to a deployed condition. For example, the interface member may initially be stowed within one of the sheaths in a non-deployed condition, and be translatable to or towards the open end of the sheath to transition to its deployed condition. In some embodiments, the interface member may be substantially freely translatable within a predetermined range of movement, and be configured to move with, or in response to, sheath movement.

Additionally or alternatively, in some embodiments, the interface member (or at least a portion thereof) may be expandable. Transition from a non-deployed condition to a deployed condition may include expansion of the expandable portion. For example, the expandable portion of the interface member may be radially expandable. The expandable portion may be self-expandable from a compressed state.

In some embodiments, the interface member may be both movable and self-expandable. For example, the interface member may initially be stowed within one of the sheaths in a compressed non-deployed condition. The sheath may constrain the interface member in a compressed condition. Relative movement between the sheath and the interface member may cause the interface member to transition towards the open end of the sheath. When the interface member is no longer constrained by the sheath, the interface member may self-expand to deploy. Upon expansion, the interface member may float or self-position at or near the open end of the sheath and/or an exposed edge of the stent-holder, in its deployed condition.

(d) The delivery catheter may comprise a sleeve or skirt (or segments) of flexible material for fitting between the outer surface of a portion of the stent-valve, and an interior surface of a translatable sheath of the delivery catheter. The sleeve/skirt segments may also be referred to as petals or tabs. The sleeve/skirt (or segments) may be of flexible film or wafer material. The sheath may translate relative to the sleeve/skirt (or segments). The sleeve/skirt (or segments) may optionally be mounted on a stent holder of the delivery catheter. The sleeve/skirt (or segments) may optionally be made from balloon material of a balloon catheter, for example, a valvuloplasty balloon catheter. Such material is strong, resistant to tearing, yet flexible.

The sleeve/skirt (or segments) may reduce friction between the sheath and the stent-valve, for example, facilitating easier loading of the stent-valve within the sheath of the delivery catheter. The sleeve/skirt (or segments) may also avoid the sheath from catching against an edge of an outer skirt of the stent-valve.

In some embodiments, the sleeve/skirt may comprise a sleeve section having a closed-loop shape at one end, and slits at an opposite end defining segments that can flex outwardly independently of each other.

(e) In further feature similar to (d), the delivery catheter may comprise a stent holder for mating engagement with a stent-valve when in a compressed state for axially restraining the stent-valve against axial movement in at least one direction, the stent holder having attached thereto a sleeve/skirt (or segments) of flexible material.

In some embodiments, the sleeve/skirt (or segments) may be configured for overlapping an outer surface portion of a stent-valve mating with the stent holder.

In some embodiments, the stent holder may comprise a radially recessed portion for receiving a portion of a stent-valve. The sleeve/skirt (or segments) may cover the radially recessed portion, at least in one position of the sleeve/skirt (or segments).

In some embodiments, the sleeve/skirt may comprise a sleeve section having a closed-loop shape at one end, and slits at an opposite end defining segments that can flex outwardly independently of each other.

In some embodiments, the sleeve/skirt may overlap substantially the entire axial length of the stent holder.

In some embodiments, the sleeve/skirt (or segments) may be made from balloon material of a balloon catheter, for example, a valvuloplasty balloon catheter. Such material is strong, resistant to tearing, yet flexible.

(f) The distal portion of the delivery catheter may comprise: at least one sheath that is translatable from a restraining position for restraining at least a portion of the stent-valve compressed, to an open position in which the respective portion of the stent-valve is uncovered for deployment; and a stent holder relative to which the at least one sheath translates. The stent holder may be configured to cooperate with the stent-valve for retaining the stent-valve in a predetermined axial position during sheath translation.

The delivery catheter may comprise a stem portion extending between the distal and proximal ends. The stem portion may comprise a first tube within which a second tube is nested. One of the first and second tubes may be coupled to the sheath, and the other to the stent holder. The first and second tubes may be relatively slidable to transmit relative motion from the proximal end to the distal end, for translating the sheath relative to the stent holder.

The second tube may be hollow to define a guide-wire lumen for receiving (directly or indirectly) a guide wire. The second tube may comprise polyamide material and polyimide material. The polyamide and polyimide may be layered one over the other to define an integral tubular laminate having a radially inner layer and a radially outer layer, for example, by coextrusion. In some embodiments, the radially inner layer may be of polyimide, and the radially outer layer of polyamide. However, in other embodiments, the order could be reversed if desired. Polyimide has a desirably high modulus and strength, but is expensive to manufacture in significant thickness. The addition of a polyamide layer can complement the physical properties of the polyimide, providing a thicker tube of high tensile and column strength, good flexibility, and high modulus. For example, the polyimide and polyamide combination can provide properties similar to far more expensive materials such as PEEK (poly-ether-ether-ketone) tubing that is sometimes used in catheter delivery systems.

The first tube may be of plastics in which is embedded a braid. The plastics may, for example, be polyamide. The braid may, for example, be of stainless steel filaments.

(g) The stem portion may comprise tubes (referred to later as first and third tubes) nested one within the other. The tubes may be of plastics in which is embedded a respective braid. The braids may be different to provide different properties. The braids may be defined by a density or PPI ("picks per inch") and/or by a braid angle. One braid (for example, for the radially outer of these tubes) may have a lower density (e.g. PPI) than the other braid (for example, for the radially inner of these tubes). The density may, for example, be at least twice, optionally at least 5 times, optionally at least 10 times, the density of the other. In one form, the radially inner of these tubes may have a PPI of between 5 and 10, for example about 8. Additionally or alternatively, the radially out of these tubes may have a PPI of between about 50 and 100, for example, about 80.

A higher density of braid may provide good column strength by virtue of the amount of braid filament embedded in the tube. A good column strength may enable transmission of a compression force axially along the tube.

A lower density of braid and/or a braid angle of about 45 degrees may provide good for good torque transmission along the length of the respective tube. The combination of two different braid densities may provide better characteristics than an identical braid in both tubes.

(h) The stem portion may comprise at least three tubes nested one within another, and defining at least two spaces (e.g. generally annular but subject to relative movement between the tubes) therebetween. The delivery catheter may further comprise a flushing port for receiving a liquid for flushing both spaces. The same flushing port may communicate with both the first and second spaces to supply the liquid directly to both the first and second spaces. Alternatively, the flushing port may communicate with one of the first and second spaces for supplying liquid thereto, and a communication channel may be provided for passing liquid from one space to the other. For example, the communication channel may be an opening in the wall of one of the tubes.

Such an arrangement can avoid having to provide a different flushing port for each space to be flushed. It can also simplify the flushing operation for an operator.

(i) The delivery catheter may comprise first and second hollow flexible tubes extending between the distal and proximal portions of the catheter. A first tube coupling may couple the first tube to a stent holder tube on which a stent holder is mounted. An end of the stent holder tube may be received within the first tube at the first tube coupling. The second tube may be nested within the first tube and translatable relative to the first tube. The second tube may be coupled (directly or indirectly) to a sheath for applying a translation force to the sheath. The second tube may provide a guide-wire receiving lumen for receiving (directly or indirectly) a guide wire. The second tube may include a distal extension having a smaller outer diameter than a main portion of the second tube, and communicating therewith at an interface point. The distal extension of the second tube may be nested within the stent holder tube, and be translatable relative to the stent holder tube (in response to relative translation forces being applied via the first and second tubes). The first tube coupling may be distal of the interface point of the second tube.

The interface point of the second tube may be spaced axially from the first tube coupling in the closed position of the sheath. The interface point of the second tube may displace relatively towards the first tube coupling as the sheath is moved towards its open position.

(j) The delivery catheter may comprise first and second flexible tubes extending between the distal and proximal portions of the catheter. A handle portion of the catheter may be operable to tension and/or "pre-tension" at least one of the flexible tubes, for example, prior to insertion into the body, and/or prior to arrival at the desired site of implantation, and/or prior to opening of a sheath. Pre-tensioning may avoid any tendency for the respective tube to further elongate when a manipulation force is applied through a neighbouring tube.

In some embodiments, the tensioned tube may be coupled to a sheath that translates distally from a closed position for restraining a portion of the stent-valve to an open position for deploying the respective portion of the stent-valve. Tensioning the tube may bias the sheath in a proximal direction, in order to restrain the sheath against distal creep when manipulation forces are applied through at least one other tube, for example, for translating open a second sheath.

The use of tension or "pre-tension" can avoid any need for a locking mechanism, or sheath overlap, or additional sheath length that might otherwise be used to counter distal creep. The use of tension can therefore provide a more compact and/or less complicated distal portion.

(k) The delivery catheter may further comprise a member (e.g. interface member) captive on the catheter, and slidable with respect to the sheath. The member may initially be stowed within the sheath, and may be displaced out of the sheath by relative movement of the sheath (e.g. between the sheath and the member). The member may be self-expandable (or include a self-expandable portion) such that, once displaced out of the sheath, the member (or portion) self-expands to become oversize compared to the sheath. The oversize member may tend to remain at least partly outside the interior of sheath.

(l) The delivery catheter may comprise a stent holder for mating engagement with a stent-valve when in the compressed state, for restraining the stent-valve against axial movement, the stent holder comprising a body having a plurality of substantially radial projections for mating with attachment elements of a stent-valve, each projection having at least one ramp surface extending partly therearound to define ramp surface portions circumferentially either side of the projection and axially to one side of the projection, the ramp surface portions inclined outwardly away from the projections.

With such an arrangement, the ramp surface portions may aid separation of the stent-valve attachment element from the stent-holder when the stent-valve is completed unsheathed for expansion to the functional state. Small axial or rotational movement of the delivery system can cause the attachment elements to ride up one of the ramp surface portions and be urged radially away from the stent holder, if the attachment element might otherwise remain in proximity to the projection.

In some embodiments, the stent holder body has a portion defined by surface of rotation in which radial recesses are provided. A respective projection may project within each recess. The radial length of the projection may be accommodated entirely or substantially within the recess. A respective ramp surface may define one axial side and opposite circumferential sides of the recess. The other axial side of the recess may be open. The recess may open radially outwardly.

Such an arrangement of stent holder may have a generally smooth outer contour provided by the surface of revolution. A smooth surface may, for example, facilitate withdrawal of the distal portion of the delivery catheter (including the stent holder) through the valve of the stent-valve following deployment of the stent-valve.

(m) The delivery catheter may further comprise a ball joint located proximal of the stent accommodation region. The ball joint may be formed in an outer tube at or leading to the distal portion.

In such a delivery catheter, the proximal portion can include a distal (first) sheath that is slidably configured to cover at least a portion of the distal end of the accommodation region and configured to slide distally to reveal the distal end of the accommodation region for the collapsible stent, and a proximal (second) sheath that is slidably configured to cover at least a portion of the proximal end of the accommodation region for the collapsible stent and to slide proximally to reveal the proximal end of the accommodation region for the collapsible stent. In some embodiments, the distal sheath and the proximal sheath meet at the proximal end of the distal sheath and the distal end of the proximal sheath when they cover the distal and proximal ends of the collapsible stent.

The ball joint can be less than 5 cm proximal of the stent accommodation region of the catheter. It can also be less than 2 cm proximal of the stent accommodation region of the catheter. It can also be less than 1 cm of the stent accommodation region of the catheter. It can also be between 1 and 2 cm proximal of the stent accommodation region of the catheter. The ball joint of the cardiac stent delivery system can also be hollow. Also, one or more inner tubular members can pass through the hollow portion of the ball joint. The ball joint can also allow the outer and inner tubular members to bend, according to some embodiments, at least 20° or at least 30° or at least 40° or at least 45°.

In some embodiments, the ball joint of the cardiac stent delivery catheter can also allow an axial force to be applied on the inner tubular member and the outer tubular member causing the distal sheath to be moved distally and/or the proximal sheath to be moved proximally. This motion of the distal sheath distally and the proximal sheath proximally can reveal the collapsible stent on the attachment region, for example.

In some embodiments, the ball joint of the cardiac stent delivery catheter can also allow the outer and inner tubular members to rotate with regards to each other. The outer and inner tubular members can be allowed to rotate with regards to each other for one rotation, or for unlimited rotations, for example.

(n) The system may comprise:

an aortic stent-valve comprising a stent component and a plurality of valve leaflets supported by the stent component, the stent component having an inflow end and an outflow end and being self-expandable from a compressed state for delivery towards a functional state upon implantation, the stent component comprising outflow structure at or towards the outflow end, a crown intermediate the inflow and outflow ends, the crown having a free extremity intermediate the inflow and outflow ends and directed towards the outflow end, and the stent-component further comprising a fixation section between the crown and the inflow end;

a delivery catheter having a distal portion for insertion into the anatomy, and a proximal portion, a stent-valve accommodation region at the distal portion for accommodating the stent-valve in the compressed state for delivery, the distal portion comprising a first sheath for covering at least a portion of the fixation section to constrain the fixation section compressed, and a second sheath for covering at least a portion of the arches and at least a portion of the crown to constrain the arches and the crown compressed.

The second sheath may be translatable in a proximal direction to uncover the crown and the outflow structure. The first sheath may be translatable in a distal direction to uncover the fixation section. Use of such sheaths moving in opposite directions can permit at least partial deployment of the crown and outflow structure without substantial distal extension of the catheter. It can also reduce the total distal extension of the catheter when the sheaths are open (compared to a catheter employing a single distally-moving sheath).

The outflow section may comprise a plurality of arches at the outflow end each having an apex at the outflow end.

Translation of the second sheath (for example, in a proximal direction) may uncover the crown for deployment followed by uncovering the outflow structure (e.g. arches) for deployment. Such a sequence is different from that described in the aforementioned WO-A-2009/053497 and WO-A-2011/051043. Nevertheless, it has been appreciated that deploying the outflow structure (e.g. arches) after the crown is still highly effective in permitting the arches to function. Notably, the outflow structure (e.g. arches) may be deployed prior to uncovering of the fixation section for deployment.

In some embodiments, the outflow structure (e.g. arches) may be configured for aligning the stent-valve with respect to an axis of the ascending aorta by contact with a wall of the ascending aorta. For example, the arches may be bendable independently of each other. The crown may be configured for engaging and/or seating against existing leaflets from an outflow side. The fixation section may be configured for engaging an existing annulus.

Deploying the outflow structure (e.g. arches) before the fixation section may permit self-alignment of the stent-valve by the action of the outflow structure (e.g. arches), before the fixation section deploys to anchor the stent-valve at the annulus of the existing valve.

Further aspects of the invention relates to methods of use of the stent-valve and/or delivery catheter by using process steps corresponding to any of those described above.

Further aspects of the invention relate to a stent-valve. Optionally, the stent-valve may be for use in a system as described above and/or for use with a delivery catheter as described above. The following definitions are therefore intended to be combined with any of the foregoing aspects. The stent-valve may comprise a valve component and a plurality of leaflets supported by the valve component. The stent-valve may further comprise any one or a combination of two of more of the following features, which are all optional:

(a) The stent component may be configured to be radially compressible into a compressed state and expandable to a functional state. The stent component may be self-expanding from the compressed state, or the stent component may be non-self-expanding (in which case the delivery catheter may comprise a device for applying an expansion force (for example, from within the stent-valve) to cause expansion). Non-limiting example materials for a self-expanding stent component include shape memory materials, especially metals alloys, such as nitinol. Non-limiting example materials for a non-self-expanding stent-component include shape memory materials, and stainless steel.

The stent component may comprise commissural supports (e.g. posts) for supporting the valve leaflets. The commissural supports may support edges of valve leaflets that meet at the commissural supports.

The commissural supports may be defined by a section of the stent component that is intermediate opposite end sections of the stent. Each commissural support may have opposite ends that each communicate with a respective stent section that is axially adjacent to the commissural support. The commissural support may optionally not have a free end.

Additionally or alternatively, the commissural supports may each have a slot for receiving a tab of a leaflet. The commissural supports may further comprise a plurality of bores flanking one or both long sides of the slot. The bores may be configured for receiving suture thread.

Additionally or alternatively, each commissural support may comprise a post. Each commissural support may have a wishbone shape. The wishbone shape may include first and second legs diverging from one end of the post.

In some embodiments, the stent component may comprise a lattice structure having at least one row of cells, the lattice structure including a sequence of cells that repeats in the circumferential direction, the sequence including cell apexes defining: a first apex node communicating at least with a first leg of a wishbone commissural support, at least one free apex spanned by the wishbone commissural post, a second node apex communicating at least with a second leg of the wishbone commissural support, and at least one further node apex communicating with an element of a crown. The first and second node apexes may communicate additionally with one or more respective elements of a crown. As mentioned above, the commissural support may comprise a post communicating at one end with the legs of the wishbone shape, and communicating at the other end with an outflow section of the stent component (e.g. comprising stabilization arches).

The above forms of construction can provide a stent that is functional to support a valve component, yet can be compressed to a small size.

(b) The stent-valve (e.g. stent component) may comprise at least one (and preferably a plurality) of attachment elements for cooperating with a stent-holder of the delivery catheter. Each attachment element (or at least one of the attachment elements) may comprise a U-shape portion joining two stent struts. The term U-shape is used herein to include any shape including a generally arcuate apex, whether or not the sides are straight or curved, bulged outwardly, parallel or non-parallel. In a collapsed (e.g. compressed) condition of the stent when received within the accommodation region of the delivery catheter, the struts may lie adjacent each other at the attachment element, such that the arc of the U-shape portion extends around a first angle more than 180 degrees to define, for example, a closed or near closed (e.g. horseshoe shape) eyelet having an aperture larger than the spacing of the struts. The horseshoe shape of the eyelet aperture and the adjacent space between the struts may together define a keyhole type shape. In an expanded (or non-collapsed) condition of the stent when released from the accommodation region of the delivery catheter, the struts may move apart, and the arc of the U-shape portion may extend around a second angle that is less than the first angle, to at least partly open the eyelet further. For example, the second angle may be about 180 degrees or less. In the expanded condition, the attached element may define a substantially straight-sided U-shape with an arcuate apex.

The delivery catheter may comprise a sent-holder provided within the accommodation region. The stent-holder may comprise (i) one or more projections receivable within the eyelet. The projection may be dimensioned such that, when the stent is in its collapsed condition, the projection is trapped within the eyelet and unable to pass between the adjacent struts, and/or (ii) one or more recesses or interstices for accommodating the eyelet substantially therewithin, at least in the collapsed state of the stent.

The above forms can provide for a compact, yet reliable and self-opening and/or self-releasing attachment between a stent-valve and a delivery system.

(c) The stent-valve may comprise at least two leaflets. The leaflets may be of pericardium tissue, most preferably porcine pericardium tissue or bovine pericardium. Porcine pericardium may provide desirable tissue thinness. Bovine pericardium may be slightly thicker but more durable.

Each valve leaflet may include at least two tabs. The tabs may serve for supporting the leaflets relative to the stent component.

In some embodiments, the tabs may be attached directly to commissural supports (e.g. posts) of the stent component. The tabs may attach to attachment means provided on the commissural support. For example, a tab may pass through a slot in a commissural support, from an interior of the stent component to an exterior. The portion of the tab exterior to the stent component may be folded to lie against the commissural support and/or sutured to the commissural support. Optionally respective tabs of two adjacent leaflets that meet at the commissural support pass through the same slot. Each tab may be folded to lie against the exterior of the commissural support without overlapping the other tab. The two tabs optionally are not directly attached to each other.

Additionally or alternatively, the leaflets may be attached to an inner skirt. The leaflets may be attached to an interior portion of the inner skirt, the tabs passing through slots (e.g., slits) in the inner skirt to the exterior of the inner skirt. The inner skirt may have scalloped clearances, each such clearance being spanned by a respective leaflet. The inner skirt may have commissural portions or upstands in which the slots (e.g., slits) are provided.

Additionally or alternatively, the material defining the inner skirt may include integral extension portions that wrap at least around the commissural supports, for covering the commissural supports and/or for covering the leaflet tabs secured to the commissural supports. The extension portions may be sutured to the commissural supports.

In some embodiments, a combination of any two or all three of the above arrangements may be used. For example, a pair of tabs of adjacent leaflets may pass through a slot in the inner skirt, and through a slot in the commissural support. The tabs may be folded back in opposite directions, and sutured to the exterior of the commissural support (optionally without the tabs being sutured directly to each other). One or more extensions of the inner skirt at the commissural support may be wrapped around the exterior of the commissural support to cover the tabs and/or the commissural support. The extension(s) may be sutured to the commissural support. For example, the sutures may pass through the same suture holes in the commissural support as those used for attaching the tabs. The extension(s) may extend axially beyond the tab(s), such that the edges of the tabs are shrouded and protected.

(d) The stent-valve may comprise a stent-component, a plurality of valve leaflets mounted within the stent component, an inner skirt attached to the valve leaflets, the inner skirt extending at least partly within the stent component, and an outer skirt extending at least partly outside the stent component. At least a portion of the stent component over which at least one of the skirts extends, may comprise a lattice structure having at least one row of a plurality of cells.

In some embodiments, the inner and outer skirts may partly overlap, at least with respect to the surface of at least one of the skirts. Additionally or alternatively, the inner and outer skirts may not have any coterminous extremity. Additionally or alternatively, the outer skirt may extend further towards an inflow extremity of the stent component than does the inner skirt. Additionally or alternatively, the inner skirt may extend further towards an outflow extremity of the stent component than does the outer skirt.

A function of the inner skirt may be to define a conduit within the stent to channel blood towards the valve leaflets, and obstruct leakage of blood through interstices of the stent component (e.g., lattice interstices). A function of the outer skirt may be to provide a seal surface outside the stent component for sealing with surrounding tissue, to obstruct leakage at the interface with surrounding tissue.

Providing both skirts may be beneficial in terms of obstructing leakage. However, the presence of both skirts can add significantly to the thickness of material carried by the stent, and thereby increase the difficulty of compressing the stent-valve to a desirably small size. By providing both skirts, with only partial overlap in an axial direction, the benefits of both skirts can be obtained, but with a reduced thickness profile in the regions where only one skirt extends. Overlapping the skirts can provide better sealing between the skirts than were the skirts to be arranged edge to edge on the interior and exterior respectively of the stent component (for example, especially bearing in mind that the stent-valve is to be deformed substantially by compression for delivery and re-expansion at implantation).

The degree of skirt overlap in the axial direction may, for example, by at least 1 mm, or at least 2 mm, or at least 3 mm, or at least 4 mm, or at least 5 mm, or at least 6 mm, or at least 7 mm, or at least 8 mm. Additionally or alternatively, the degree of skirt overlap in the axial direction may, for example, be less than 10 mm, or less than 9 mm, or less than 8 mm, or less than 7 mm, or less than 6 mm, or less than 5 mm, or less than 4 mm. For example, the degree of skirt overlap in the axial direction may be about 4-6 mm.

At least one of the skirts (optionally each skirt) may extend a non-overlapped axial distance of at least 1 mm away from the region of overlap. The non-overlapped distance for the or each skirt may, for example, be at least 2 mm, or at least 3 mm, or at least 4 mm or at least 5 mm or at least 6 mm, or at least 7 mm or at least 8 mm or at least 9 mm, or at least 10 mm.

In some embodiments, the inflow end or edge of the stent component may have a zig-zag shape defined by a lattice structure of at least one row of cells. The zig-zag shape may define an alternating sequence of free apexes (e.g., at an inflow extremity), and connected apexes (e.g. connected to lattice structure extending away from the inflow end towards the outflow end). In some embodiments, the inner skirt may extend only to the connected apexes. The outer skirt may overlap the inner skirt and extend further than the inner skirt, to a level corresponding to at least some of the free apexes.

In some embodiments, the inner skirt may be attached to an inflow edge and/or an outflow edge of valve leaflets. The inner skirt may extend towards the inflow extremity of the stent component. The outer skirt may overlap only partly the inner skirt while remaining spaced from an uppermost edge of the inner skirt. The outer skirt may extend towards (or optionally to) the inflow extremity of the stent component. The outer skirt may optionally not overlap (e.g., directly or indirectly through the stent component) any portion of the leaflets.

The inner skirt and/or outer skirt may be of any suitable material, such as pericardial tissue (e.g. porcine pericardium for thinness), PET, Dacron, etc. The inner and outer skirts may optionally be made of the same material as each other.

Additional aspects of the invention are defined in the claims. Although certain features and ideas have been highlighted above and/or in the claims, protection is claimed for any novel feature or idea described herein and/or illustrated in the drawings whether or not emphasis has been placed thereon.

Preferred embodiments of the invention are now described, by way of example only, with reference to the accompanying drawings, in which.

Figure 10:
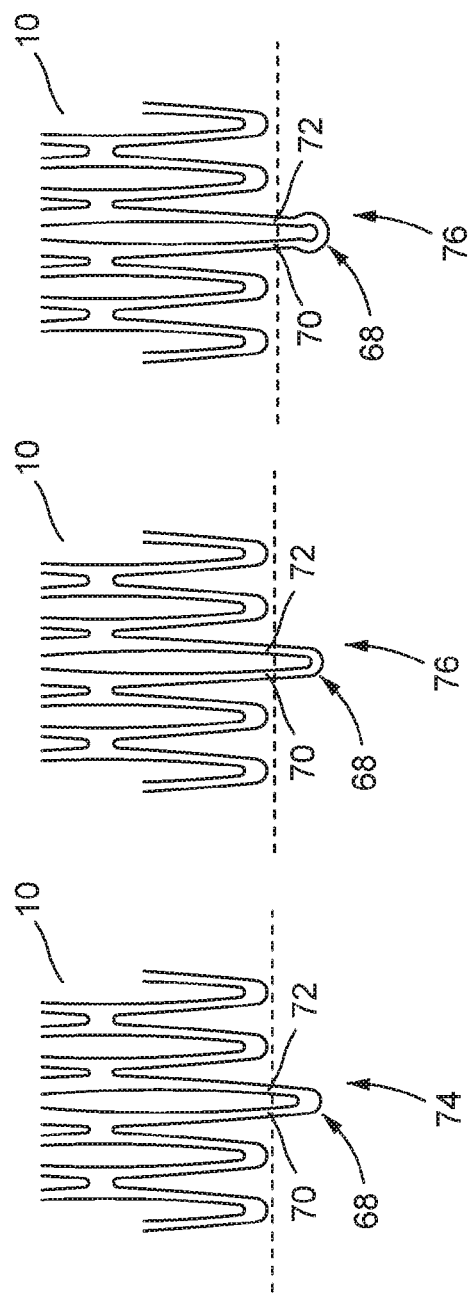
Figure 11:
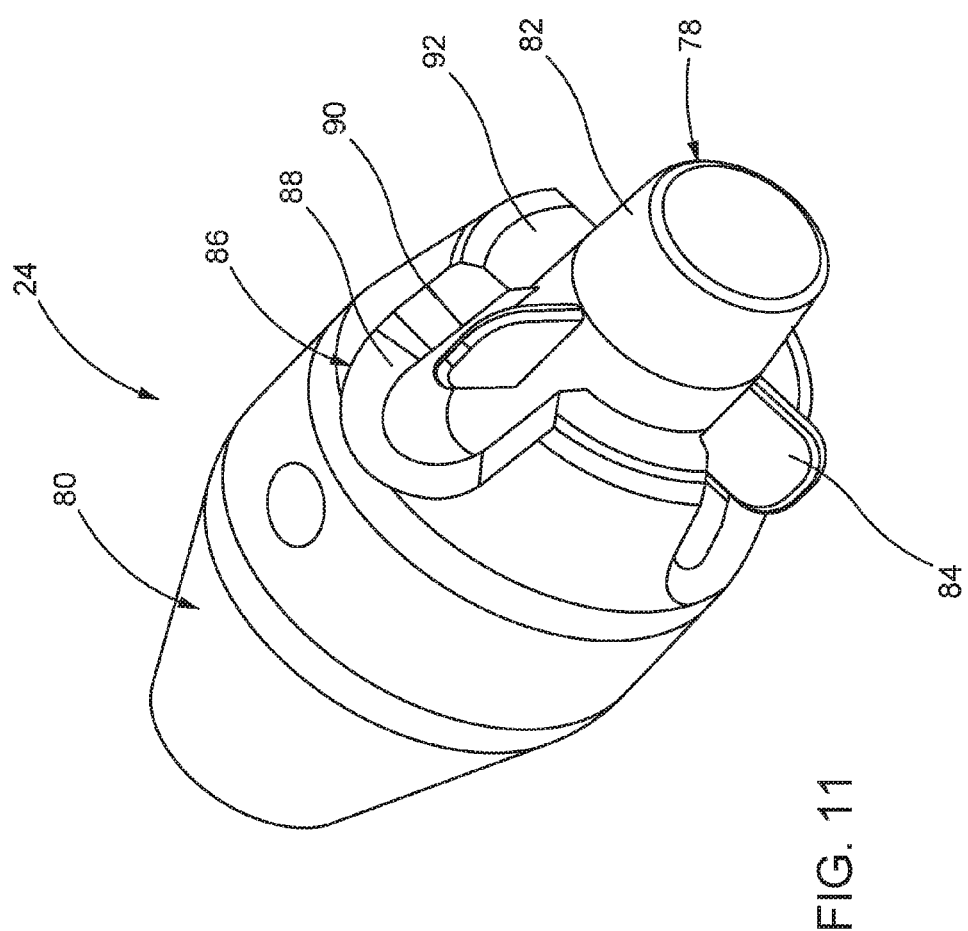
Figure 12:
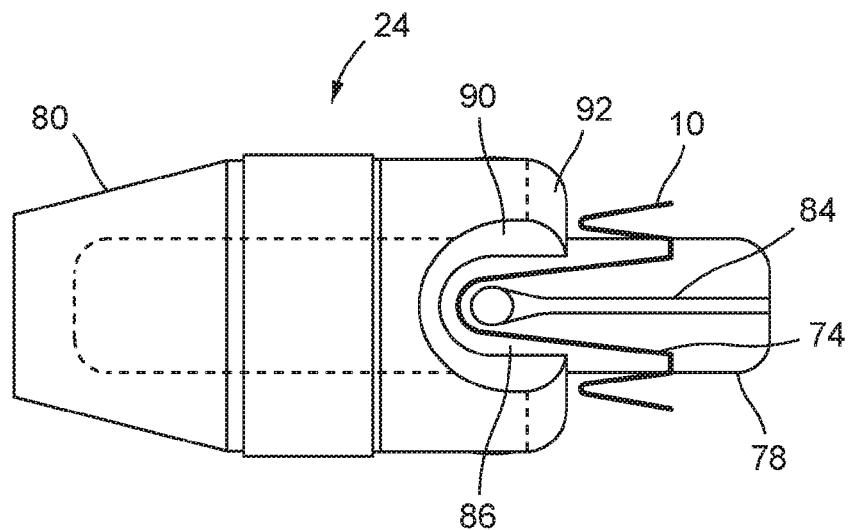
Figure 13:
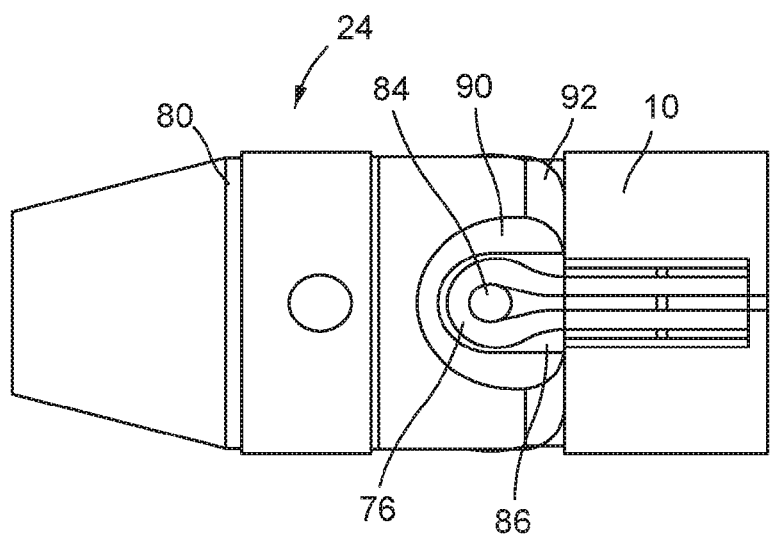
Figure 14:
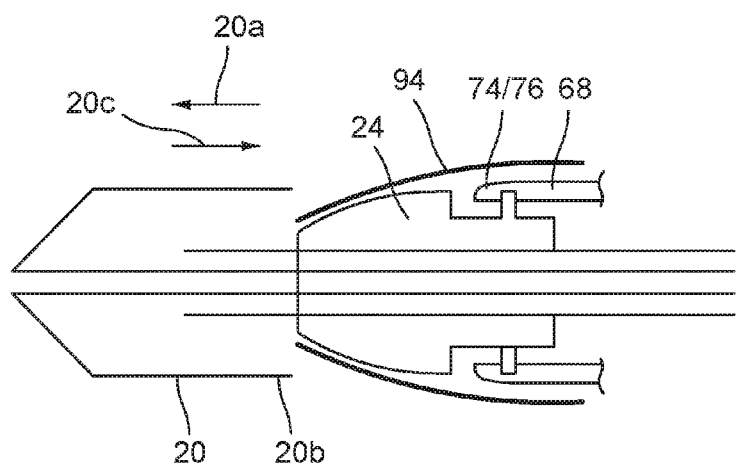
Figure 15:
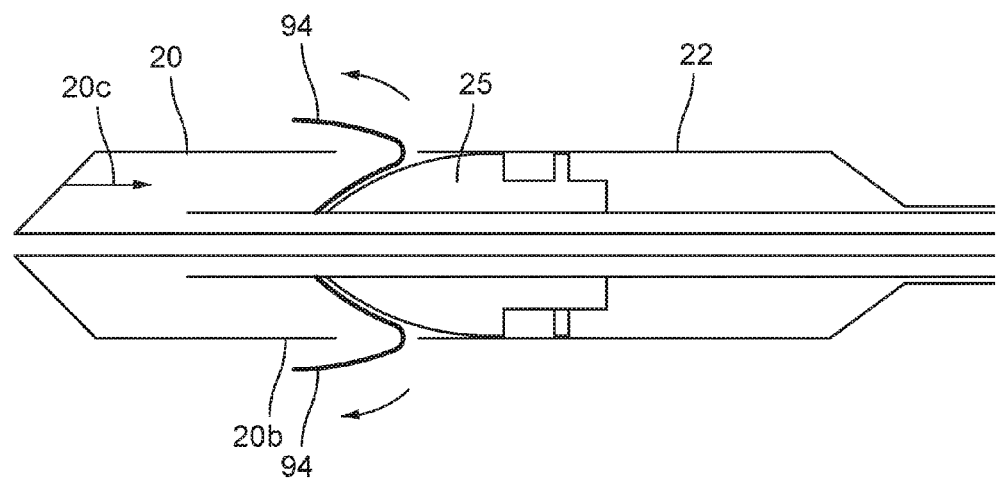
Figure 16:
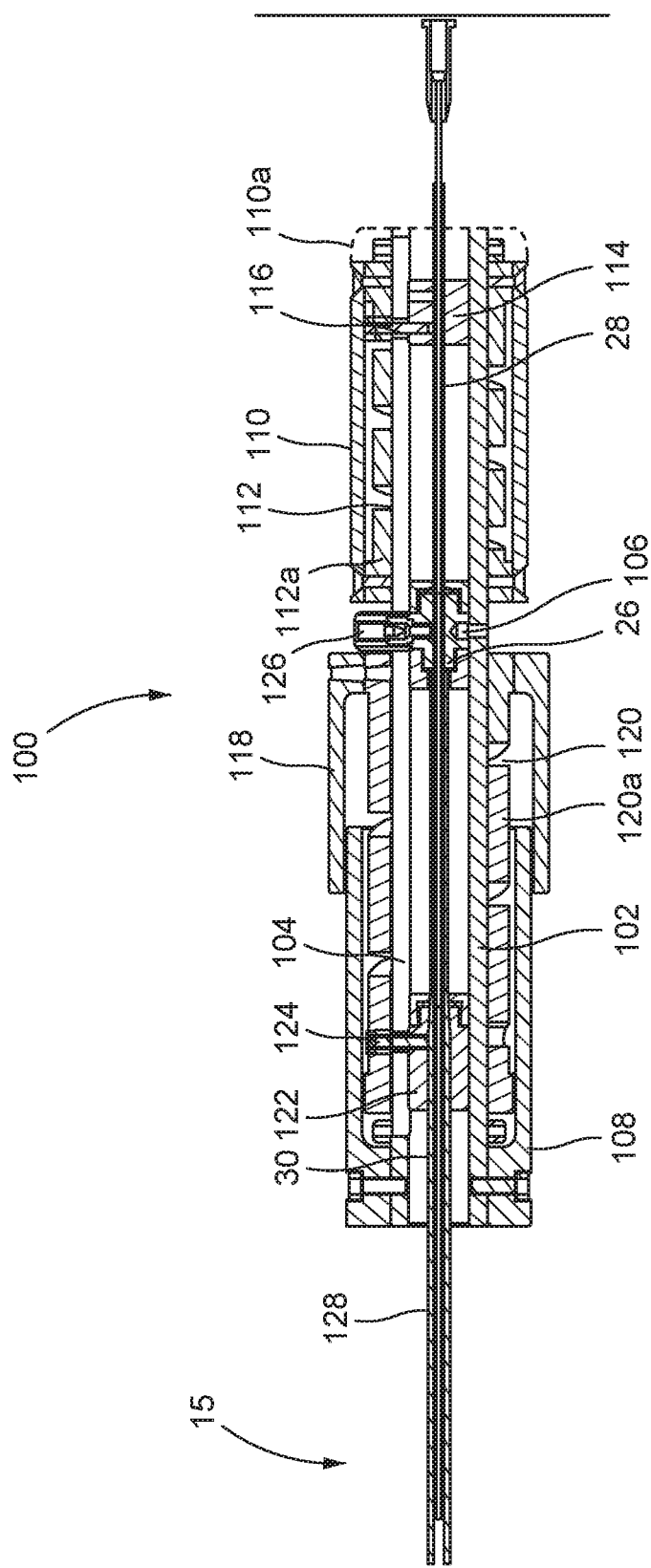
Figure 17:
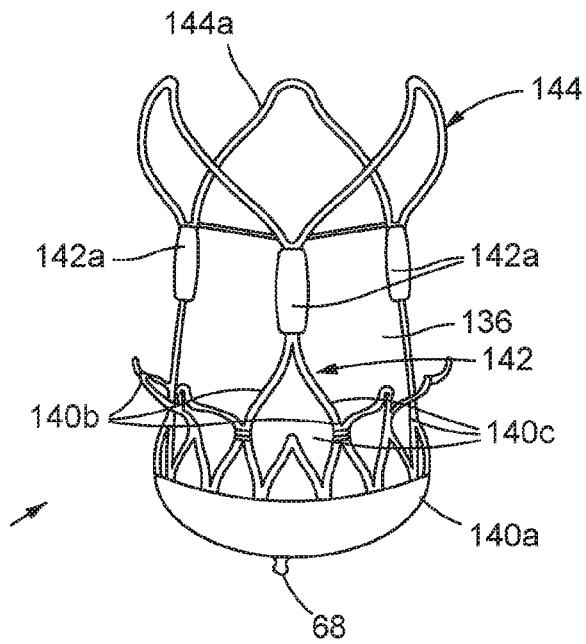
Figure 18:
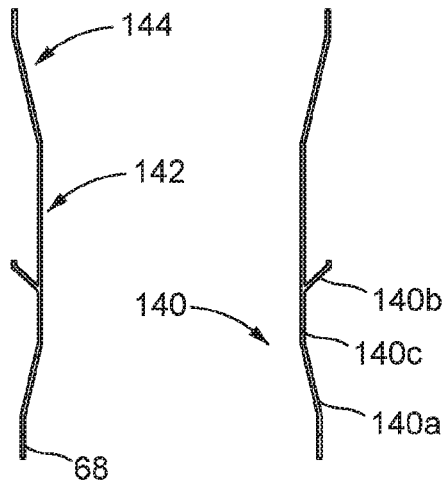
Figure 19:
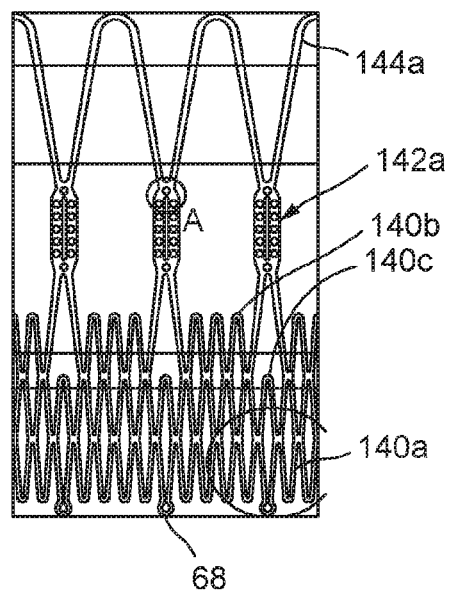
Figure 20:
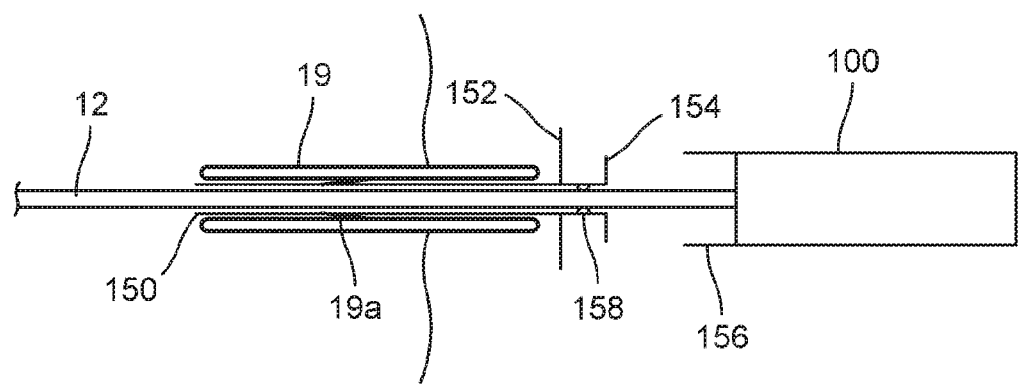
Figure 21:
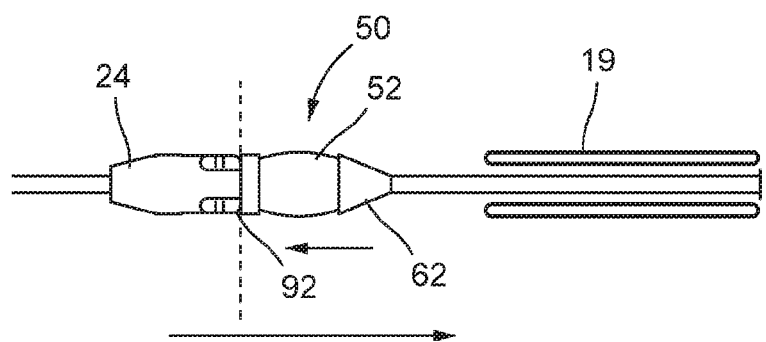
Figure 22:
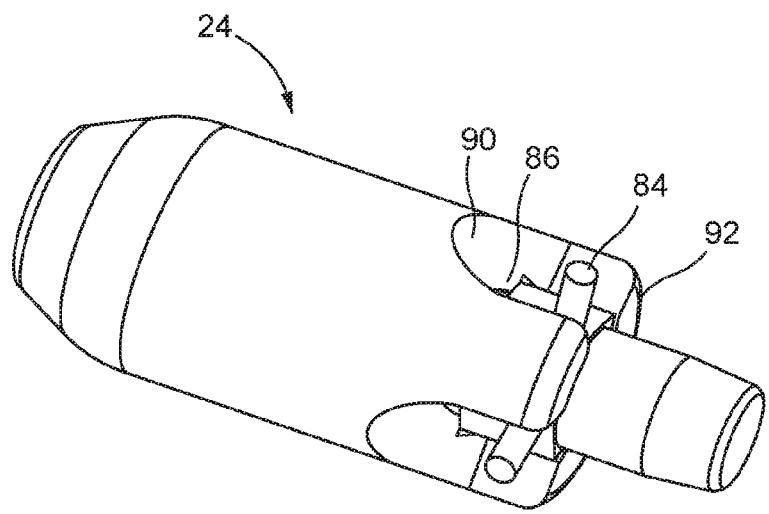
Figure 23:
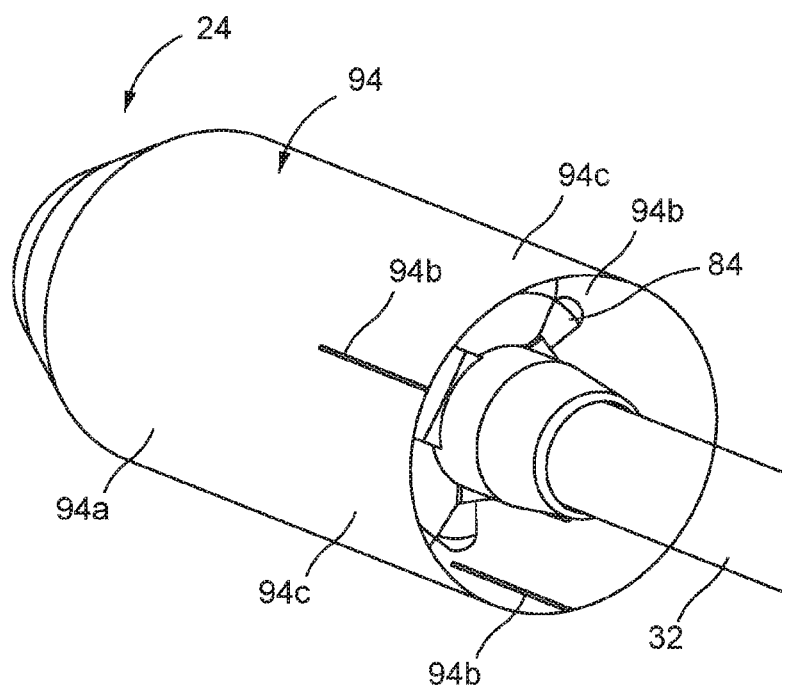
Figure 24:
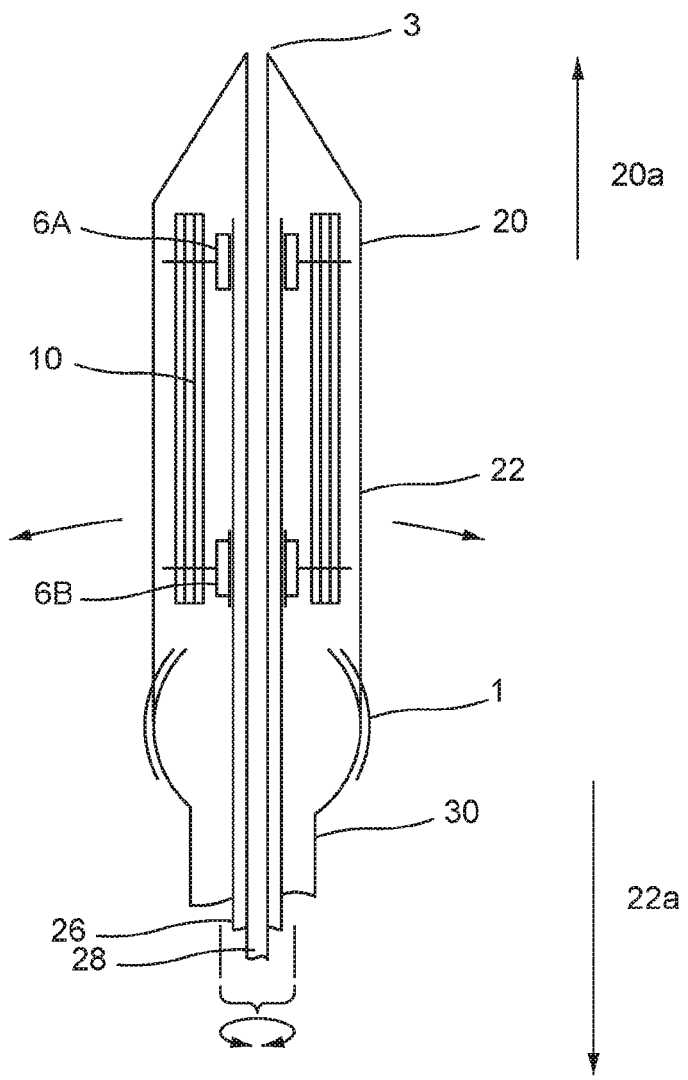

FIGS. 10a-c are schematic sections showing in isolation example attachment elements of a stent-valve for attachment to a stent-holder of the delivery catheter. The attachment elements are shown in an expanded condition of the stent-valve;

FIG. 11 is a schematic perspective view showing in isolation one example of a stent holder for the delivery catheter;

FIG. 12 is a schematic side view illustrating engagement between the attachment element of FIG. 10a and the stent holder of FIG. 11;

FIG. 13 is a schematic side view illustrating engagement between the attachment elements of FIGS. 10a/10b and a second example of stent holder;

FIG. 14 is a schematic perspective section illustrating petals on the stent holder;

FIG. 15 is a schematic section similar to FIG. 14 illustrating a combined stent holder and interface element;

FIG. 16 is a schematic section illustrating a handle with controls at the proximal end of the deliver catheter; and FIG. 17 is a schematic side view illustrating one example of stent-valve;

FIG. 18 is a schematic profile view illustrating the profile envelope of the stent component of the stent-valve of FIG. 17;

FIG. 19 is a schematic view illustrating a developed geometry of the stent component in a single plane;

FIG. 20 is a schematic section illustrating a liner sleeve for the catheter;

FIG. 21 is a schematic section illustrating the interface member for streamlining the stent holder to permit withdrawal of the catheter through an introducer while open. In FIG. 21, the sheaths are omitted to avoid clutter;

FIG. 22 is a schematic perspective view of a stent holder in isolation, as a single-piece item having a geometry similar to FIG. 13;

FIG. 23 is a schematic perspective view of the stent holder of FIG. 22 with a sheath thereon, and mounted on the stent holder support tube; and FIG. 24 is a schematic section illustrating a delivery catheter with a ball joint.

In the drawings, the same reference numerals are used to denote the same, or equivalent, features amongst different embodiments and examples. Unless described to the contrary, the description of a feature in one embodiment or example may also apply to the same or equivalent feature in another embodiment or example. Features may also be interchanged between embodiments as desired.

Figure 1:
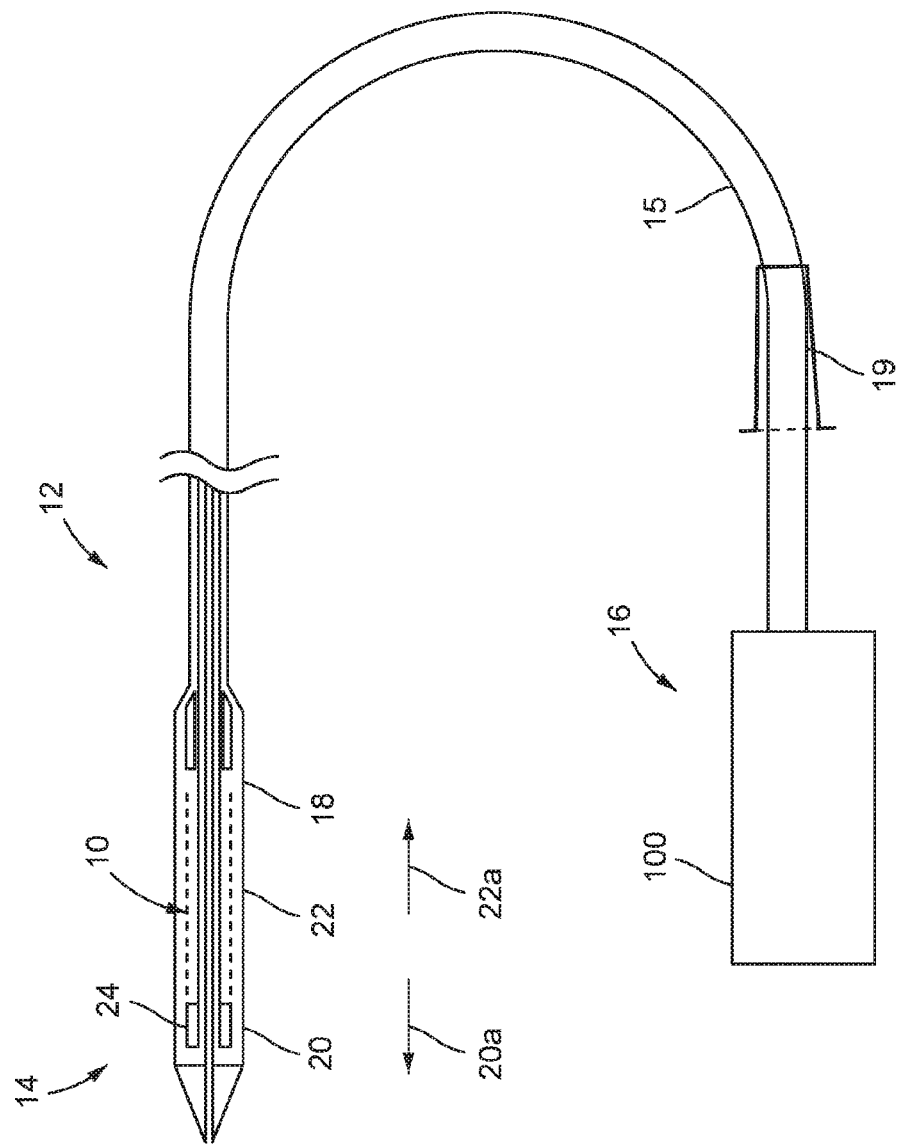
FIG. 1 is a schematic partial section view of a delivery catheter and stent-valve.
Figure 2:
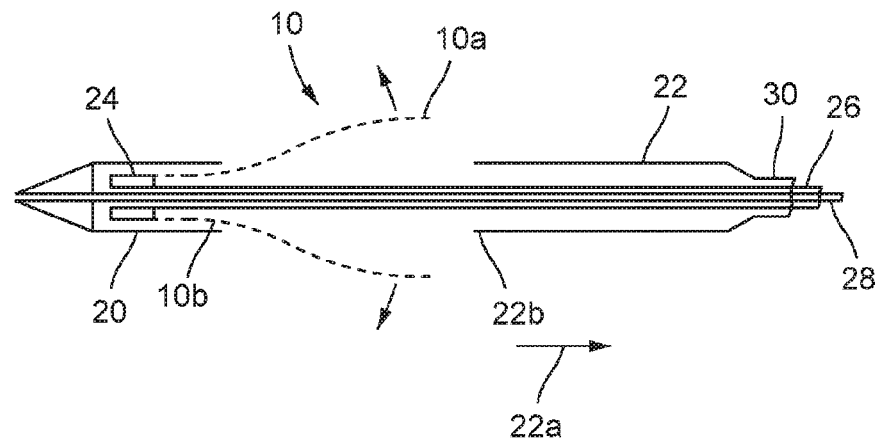
FIG. 2 is a schematic section showing the distal portion of the delivery catheter partly open.
Figure 3:
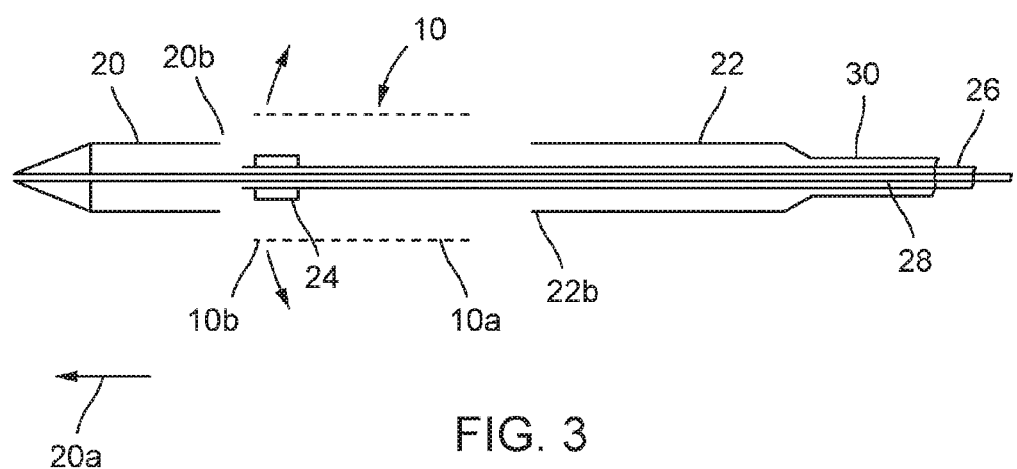
FIG. 3 is a schematic section showing the distal portion of the delivery catheter full open.

Referring to FIGS. 1-3, a stent-valve 10 and a delivery catheter 12 therefor are illustrated. The delivery catheter 12 may have a distal portion 14 towards one end for insertion into a patient's anatomy, and a proximal portion 16 towards an opposite end from which the delivery catheter is manipulated in use by an operator. A barrel or stem portion 15 may extend between the distal and proximal portions.

As used herein, the terms "distal" and "proximal" for the delivery catheter may refer to relative position with respect to an operator.

The distal portion 14 of the catheter 12 may comprise an accommodation region 18 for accommodating the stent-valve 10 in a collapsed form for introduction into the anatomy. The stent-valve 10 may be a cardiac stent-valve. The delivery catheter 12 may be configured to permit delivery of the stent-valve 10 to, and deployment at, a desired site of implantation while the heart remains beating, for example, using a minimally invasive surgical and/or percutaneous procedure. In some embodiments, the catheter 12 may be configured for introduction into the anatomical vascular system, and for advancement along the vasculature system to the desired site of implantation. For example, the catheter 12 may be configured for introduction into the femoral artery, and guided retrograde via the descending aorta, aortic arch, and ascending aorta to the heart (sometimes called a transfemoral access). The catheter 12 may have a length of at least about 1 m to provide sufficient length insertable into the anatomy. In other embodiments, the catheter 12 may be insertable via the subclavian artery and guided retrograde to the heart (sometimes call transubclavian access). In other embodiments, the catheter 12 may be inserted directly into a chamber of the heart such as a ventricle (for example, left ventricle) via a direct access route while the heart remains beating. For example, a direct access route may be through an aperture opened in the apex of the heart (sometimes called a transapical access).

The size of access aperture into the anatomy may depend on the outer diameter of the distal portion 14. The barrel portion 15 may be slightly smaller than, or the same diameter as, the distal portion 14 as desired. For minimally invasive surgery, it is desired that the access aperture into the anatomy be as small as practical, bearing in mind the size to which the stent-valve 10 can be collapsed without risk of damage. An introducer 19, for example, a standard arterial introducer, may optionally be used at the access aperture into the anatomy. The optional introducer 19 may have a size of 20 French or smaller, for example, 18 French or smaller. The distal portion 14 may be dimensioned for insertion through such a size of introducer 19.

The stent-valve 10 may be expandable from a compressed or collapsed condition to a functional and/or expanded condition, in order to anchor the stent-valve 10 at the implantation site. For example, the stent-valve 10 may form a friction and/or interference fit with respect to the native anatomy. Various shapes and geometries of stent-valve 10 may be used to fit the anatomy at the site of implantation. A generally cylindrical stent-valve 10 is illustrated here for clarity, but the invention is not limited to a cylindrical shape, and may be especially advantageous with non-cylindrical shaped stent-valves 10. A more detailed example of stent-valve 10 is described later, and all details of the delivery catheter 12 are explicitly applicable to the stent-valve shape described later.

The stent-valve 10 may be self-expanding and/or may be configured to be expandable by swelling of an expander (for example, a balloon not shown). Self-expanding stent-valves 10 may be constructed from, or use, shape-memory material, for example a shape-memory metal alloy (such as nitinol). A self-expanding stent-valve 10 may be retained in its compressed state by being constrained within a sheath 20/22 of the delivery catheter 12. Upon at least partial release from the sheath 20/22, the released portion of the stent-valve 10 may be free to expand. Non-self-expanding stent-valves 10 may also be made of shape-memory material, or from stainless steel, or cobalt-chromium alloy. A non-self-expanding stent-valve 10 may also be contained at least partly within a sheath 20/22 to protect the stent-valve 10 and/or facilitate smooth introduction through the anatomy.

The distal portion 14 of the catheter 12 may comprise at least one sheath 20 and/or 22 that is translatable between a closed position at least partly covering the accommodation region 18 and/or the stent-valve 10 therein, and an open position at least partly opening or exposing the accommodation region 18 and/or at stent-valve 10 therein. In the present example, the catheter 12 comprises two sheaths 20 and 22, both shown in their respective closed positions in FIG. 1 to at least partly (optionally substantially entirely) cover the stent-valve 10 in the accommodation region 18. The sheaths 20 and 22 may be translatable in opposite directions to respective open positions. A first (e.g. more distal) of the sheaths 20 may be translatable in a distal direction (indicated by arrow 20a in FIG. 1) to an open position (FIG. 3). The first sheath 20 may also be referred to as the distal sheath. A second (e.g. more proximal) of the sheaths 22 may be translatable in a proximal direction (indicated by arrow 22a in FIG. 1) to an open position (FIGS. 2 and 3). The second sheath 22 may also be referred to as the proximal sheath. Use of first and second opposed sheaths 20 and 22 may provide good versatility for release of the stent-valve 12 from the accommodation region. For example, referring to FIG. 2, by translating the second sheath 22 to or towards its open position without translating the first sheath 20, a portion 10a of the stent-valve 10 previously covered by the second sheath 22 may be released (at least partly) before a portion 10b of the stent-valve 10 covered by the first sheath 20. The portion 10b may be released subsequently by translation of the first sheath 20 to or towards its open position (FIG. 3). The length of the second sheath 22 may be greater than the length of the first sheath 20. For example, the ratio of the second sheath length divided by the first sheath length may be at least 1.1, optionally at least 1.2, optionally at least 1.3, optionally at least 1.4, optionally at least 1.5, optionally at least 1.6, optionally at least 1.7, optionally at least 1.8, optionally at least 1.9, optionally at least 2.0, optionally at least 2.1, optionally at least 2.2, optionally at least 2.3, optionally at least 2.4, optionally at least 2.5, optionally at least 2.6, optionally at least 2.7, optionally at least 2.8, optionally at least 2.9, optionally at least 3, optionally at least 3.5, optionally at least 4 or optionally at least 4.5, or optionally at least 5. Use of a relatively short first sheath 20 may reduce risk of trauma in use. The first sheath 20 advances distally along a path that may be less controlled than the second sheath that benefits from a more controlled path defined by the path adopted by the barrel portion 15 of the catheter. For example, in the case of transvascular access (e.g. transfemoral access), the first sheath 20 may advance into the ventricle of the heart. Use of a relatively short first sheath 20 may reduce the degree to which the catheter 12 has to penetrate into the ventricle, and risk interfering with delicate tissue surfaces. In the case of direct access (e.g. transapical access), the first sheath 20 may advance into the ascending aorta. Use of a relatively short first sheath 20 may reduce the degree to which the first sheath 20 has to penetrate the space of the ascending aorta, and risk interfering with the aorta wall.

One or both of the sheaths 20 and 22 may be of plastics optionally including reinforcement to resist radial expansion of the sheath. One suitable plastics is a poly ether block amide (PEBA), for example PEBAX (TM). Reinforcement may be provided by a helical coil embedded within the sheath. The helical coil may be of metal, for example, stainless steel filament.

The sheaths 20 and 22 may have the same inner and/or outer diameter. The sheaths 20 and 22 may be configured not to overlap each other. Avoiding an overlap can avoid excess diameter of the distal portion that might otherwise be caused by the sheath walls overlapping each other.

The sheaths 20 and 22 may be capable of being positioned such that the sheaths 20 and 22 meet substantially end to end. Alternatively, the sheaths 20 and 22 may be configured such that the sheaths 20 and 22 always remain spaced from each other, even in mutually closed positions of the first and second sheaths 20 and 22. For example, the minimum spacing may be at least 1 mm, or at least 2 mm, or at least 3 mm, or at least 4 mm, or at least 5 mm, or at least 6 mm. Additionally or alternatively, the spacing may be less than 10 mm, or less than 9 mm, or less than 8 mm, or less than 7 mm, or less than 6 mm, or less than 5 mm. In one form, the spacing is between about 4 mm and about 6 mm.

During the translations of the sheaths 20 and 22 a stent-holder 24 may retain the stent-valve 10 axially in position and/or restrain the stent-valve 10 against axial movement. The stent-holder 24 is represented purely schematically in FIGS. 1-3, and is described in more detail later. The stent-holder 24 may prevent and/or obstruct any tendency of the stent-valve 10 to be dragged by translation of a sheath 20 or 22. Additionally or alternatively, the stent-holder 24 may prevent and/or obstruct any tendency for a self-expanding stent-valve 10 to jump free of the catheter if only a small portion of the stent-valve 10 remains constrained by the sheath 20 or 22. The stent holder 24 may be positioned in the accommodation region 18 at a position appropriate to engage the stent-valve 10 until final release of the stent-valve 10 from the accommodation region. In the illustrated example, a distal portion of the stent-valve 10 may be intended to be released last, and the stent-holder 24 may be positioned towards the distal end of the accommodation region 18. In other embodiments, if the proximal portion of the stent-valve 10 is intended to be released last, the stent-holder 24 could instead be positioned towards the proximal end of the accommodation region 18.

Figure 4:
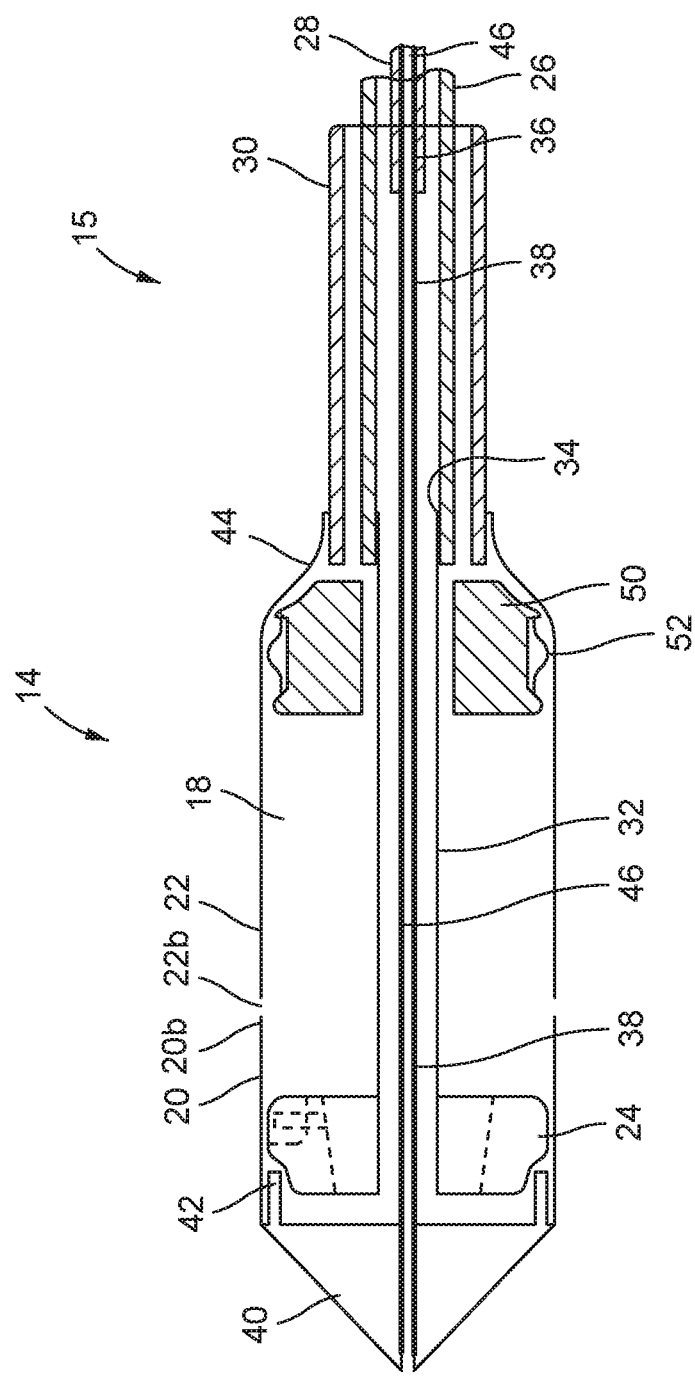
FIG. 4 is a schematic section showing the distal portion of the delivery catheter in more detail. The axial (horizontal) scale is compressed relative to the radial (vertical) scale to permit all elements to be shown in a single view.
Figure 5:
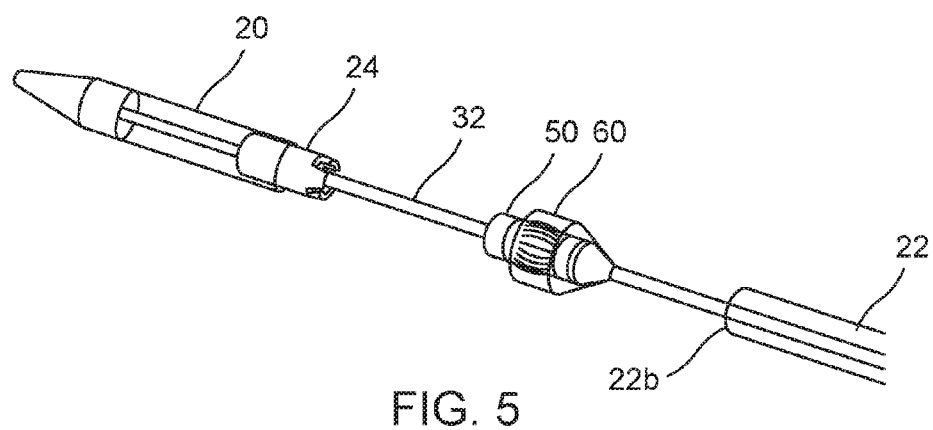
FIG. 5 is a schematic perspective view showing the distal portion of the delivery catheter full open deploying the interface element.
Figure 6:
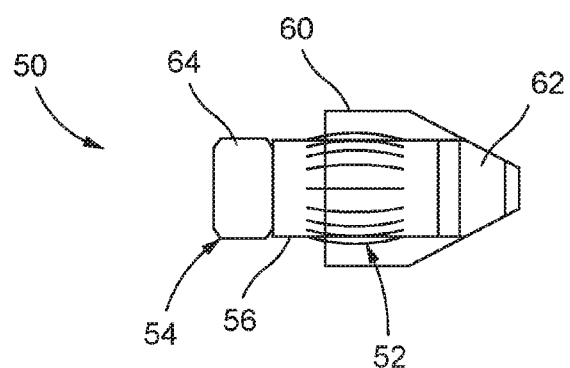
FIG. 6 is a schematic side view of the interface element in isolation, shown in a deployed condition.
Figure 7:
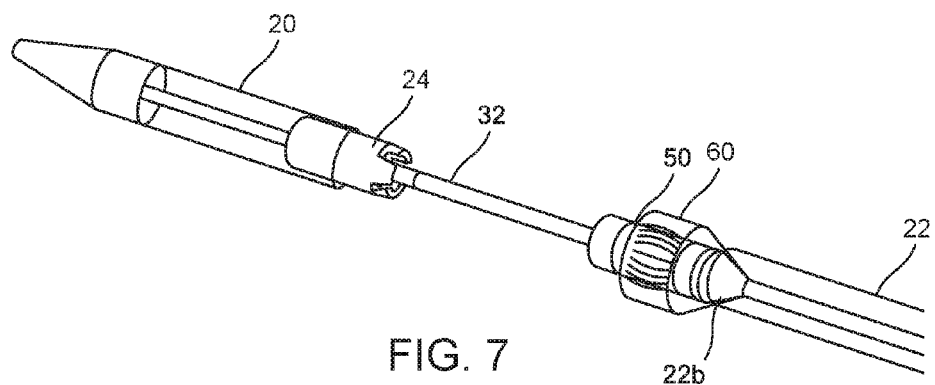
FIG. 7 is a schematic perspective view showing the initial closing of the second sheath.
Figure 8:
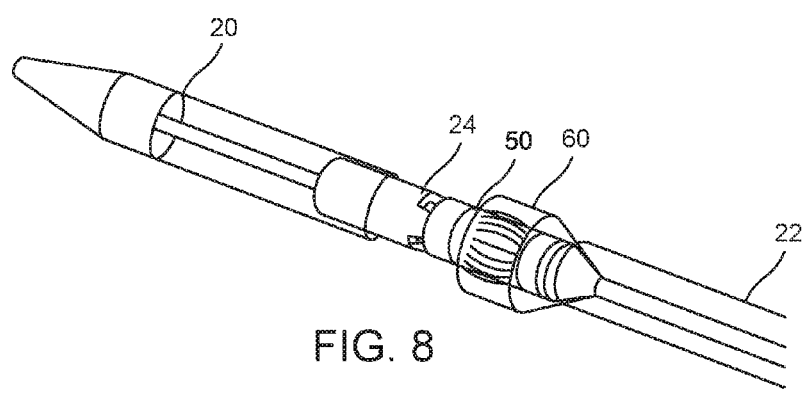
FIG. 8 is a schematic perspective view showing the second sheath in its closed position.
Figure 9:
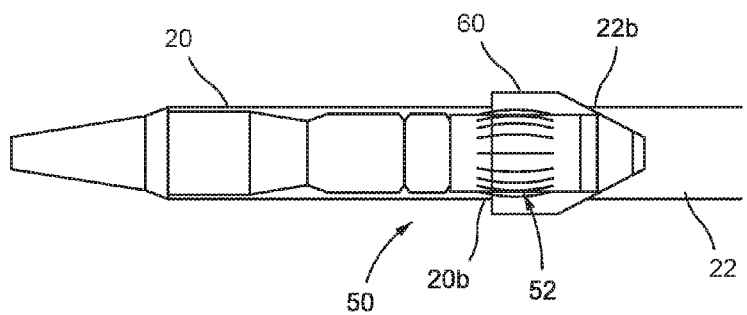
FIG. 9 is a schematic side view showing the first and second sheaths reclosed with the interface element deployed.

FIG. 4 illustrates one example construction of the distal portion 14 of the catheter 12 in more detail. The barrel portion 15 comprises a plurality of flexible tubes 26, 28 and 30 extending between the distal portion 14 and the proximal portion 16. The tubes 26-30 may be nested at least one within another, and coupled to the sheaths 20 and 22 and the stent holder 24. The sheaths 20 and 22 may be translated by relative translation of respective tubes. At least one, optionally two, optionally three, optionally more, of the flexible tubes may be of plastics, optionally with reinforcement.

For example, at least one tube may comprise a combination of polyamide material and polyimide material. The polyamide and polyimide may be layered one over the other to define an integral tubular laminate having a radially inner layer and a radially outer layer, for example, by coextrusion. In some embodiments, the radially inner layer may be of polyimide, and the radially outer layer of polyamide. However, in other embodiments, the order could be reversed if desired. Polyimide has a desirably high modulus and strength, but is expensive to manufacture in significant thickness. The addition of a polyamide layer can complement the physical properties of the polyimide, providing a thicker tube of high tensile and column strength, good flexibility, and high modulus. For example, the polyimide and polyamide combination can provide properties similar to far more expensive materials such as PEEK (poly-ether-ether-ketone) tubing that is sometimes used in catheter delivery systems.

Additionally or alternatively, reinforcement may be provided by a braid, for example, a metal braid, within the plastics. The plastics may, for example, be a polyamide, and/or the braid of stainless steel filament. The reinforcement may, compared to a tube of the same plastics without the reinforcement: (i) increase the modulus of elasticity yet retain flexibility; and/or (ii) improve resistance to kinking when the tube is flexed; and/or (iii) increase the ability for transmission of torque from the proximal portion to the distal portion. Respective different tubes may have respective different braids. The braids may be defined by a density or PPI ("peaks per inch") and/or by a braid angle. For example, a lower density may imply that the winding angle is closer to the axial direction; a higher density implies that the winding angle is closer to the radial direction. One braid (for example, a more radially outer tube) may have a lower density (e.g. PPI) than another braid (for example, for a more radially inner tube). The density may, for example, be at least twice, optionally at least 5 times, optionally at least 10 times, the density of the other. A higher density may provide for greater column strength. A lower density and/or a braid angle closer to 45 degrees may provide for greater torque transmission. The combination of two different braid densities may provide better characteristics than an identical braid in both tubes. In some embodiments, one tube may have a braid PPI of between about 5 and about 10, for example, about 8. Additionally or alternatively, the other tube may have a braid PPI of between about 50 and about 100, for example, about 80.

Referring to the specific structure in FIG. 4, a first tube 26 may be coupled for controlling the stent holder 24. The first tube 26 may optionally comprise plastics with braid reinforcement, as described above. A first tube coupling 34 may couple the first tube 26 to a stent holder support tube 32 on which the stent holder 24 is mounted. For example, the stent holder support tube 32 may be inserted into the end of the first tube 26 and/or attached thereto, at the first tube coupling 34. The stent holder support tube 32 may have a smaller outer diameter than the first tube 26. The stent holder support tube 32 may be less flexible than the first tube 26. The stent holder support tube 32 may, for example, be of polyimide. The stent holder support tube 32 may act as an extension of the first tube 26 adapted to pass within the relatively confined space of the accommodation region 18. The reduced flexibility can compensate for smaller diameter to provide adequate column strength along the axis of the stent holder support tube 32.

A second tube 28 may be coupled to control the first (distal) sheath 20. The second tube 28 may optionally comprise a tubular laminate of a polyimide layer radially within a polyamide layer, including any of the associated details described above. The second tube 28 may be nested within the first tube 26 and be translatable relative thereto. The second tube 28 may include a distal extension 38 having a smaller outer diameter than a main portion of the second tube, and communicating therewith at an inter-face point 36. The distal extension 38 may, for example, be an extension of the polyimide inner layer without the polyamide outer. The distal extension 38 may support (directly or indirectly) the first sheath 20. The sheath 20 is mounted to the distal extension 38 by a tip member 40. The tip member 40 may have a tapered atraumatic shape to aid advancement of the catheter 12 within the anatomy without trauma to the surrounding anatomy. The tip member 40 may have a rear extension 42 around which the first sheath 20 is attached immovably to the tip member 40. The smaller outer diameter of the distal extension 38 may be configured to pass within the small diameter of the stent holder support tube 32. The distal extension 38 may translate within the stent holder support tube 32, and move therewithin as the second tube 28 moves within the first tube 26. To move the first sheath 20 to its open position, a translation force may be applied to advance the second tube 28 distally relative to the first tube 26. The translation force and movement is applied from the second tube 28 to the distal extension 38, which pulls the first sheath 20 distally (for example, the translation force and movement being applied through the tip member 40). Concurrently, the stent holder 24 may hold the stent-valve 10 relatively stationary under the control of the first tube 26 and the stent holder support tube 32 on which the stent holder 24 is mounted.

The optional diameter difference between the first tube 26 and the stent holder support tube 32 may define a profile step or change at the first tube coupling 34. The optional diameter difference between the second tube 28 and the distal extension 38 may define a profile step or change at the interface point 36. The outer diameter of the second tube 28 may be greater than the inner diameter of the stent holder support tube 34 (for example such that the second tube cannot translate beyond the first tube coupling 34). In the closed position of the first sheath 20, the first tube coupling 34 and the interface point 36 may be spaced apart. The interface point 36 may be proximal of the first tube coupling 34. The spacing may be at least as large as the amount of linear translation of the first sheath 20 when the sheath moves between its open and closed positions. The spacing may permit the interface point 36 to advance distally.

The second tube 28 and the distal extension 38 may define a lumen 46 extending through the catheter. The lumen 46 may be a guidewire receiving lumen for receiving a guide wire (not shown) along which the catheter 12 may be advanced within the anatomy to guide the distal portion 14 to the desired site of implantation.

A third tube 30 may be coupled for controlling the second (proximal) sheath 22. The third tube 30 may optionally comprise plastics with braid reinforcement, as described above. The first tube 26 may be nested with the third tube 30. The third tube may be translatable relative to the first tube 26 and/or the second tube 28. A third tube coupling 44 may couple the third tube 30 to the second sheath 22. The third tube coupling 44 may include a tapered surface for defining a smooth atraumatic transition between the outer surfaces of the third tube 30 and the second sheath 22. The third tube coupling 44 may be integral with the second sheath 22, and may be a narrowed end portion thereof.

To move the second sheath 32 to its open position, a translation force (e.g. tension) may be applied to retract the third tube 30 proximally relative to the first tube 26. The translation force and movement is applied from the third tube 30 to the second sheath 22, which pulls the second sheath 22 proximally. Concurrently, the stent holder 24 may hold the stent-valve 10 relatively stationary under the control of the first tube 26 and the stent holder support tube 32 on which the stent holder 24 is mounted.

As described above, the braids in the first and third tubes 26 and 30 may have different characteristics according to their respective inner and outer radial relationship.

The sequential order in which the first and second sheaths are translated to their open position may depend on the design of the stent-valve. In at least some embodiments, the second sheath 22 may be translated before the first sheath 20. An example deployment sequence is described later.

Also, in some embodiments, at least one of the tubes may be pre-tensionable at least prior to opening the distal potion 14 for deploying a stent-valve. Pre-tensioning the tube may compensate for any tendency of the portion of the catheter controlled by the tube to creep distally in response to forces applied during manipulation to open other portion(s) of the catheter controlled by other tube(s). For example, the second tube 28 may be pre-tensioned from the proximal end, in order to prevent the first sheath 20 from creeping distally when the second sheath 22 is pulled back while applying a maintaining force to the first tube 26. Creeping of the first sheath 20 is undesirable as it may result in movement of the deployment position, or premature release of the stent. Pre-tensioning the second tube 28 may maintain the first sheath 20 firmly closed, thereby preventing premature release. When it is desired to open the first sheath 20 by applying a pushing force through the second tube 28, the pre-tension is removed as part of the transition to applying a pushing force. The pre-tension may be generated by controls within the handle, as described later. The amount of pre-tension may be sufficient to counter the reaction force applied through the first tube when translating the third tube to move the second sheath proximally. The amount of pre-tension appropriate for a specific embodiment of delivery catheter may, for example, be derivable empirically.

The above arrangements can provide a delivery catheter that combines the desirable properties of compact size, good flexibility without kinking, good transmission of torque, good column strength, and avoidance of distal creep of a sheath, all without using exotic materials that are prohibitively expensive.

Where additional flexibility is desired, the invention also contemplates inclusion of a ball joint (not shown) that is just proximal of the distal portion. The ball joint may be provided in the third tube, or the connecting portion between the third tube and the second sheath. The ball joint may be hollow to allow the first and second tubes to pass therethrough.

As may be seen generally in FIGS. 1-4, the first and second sheaths 20 and 22 may have respective mouths or open ends 20b, 22b, respectively, that may generally confront or lap one another when the (or each) sheath 20, 22 is in the closed position, or may remain slightly spaced apart. In the illustrated embodiments, both sheaths 20 and 22 are translatable, but in some embodiments it is possible that only one of the sheaths 20 and 22 might be translatable.

Prior to release of the stent-valve 10, the presence of the stent-valve 10 within the accommodation region 18 may cause the sheaths 20 and 22 to be generally aligned in register. Even if the open ends 20b and 22b are spaced from each other or confront each other without lapping, the open ends 20b and 22b may thus align in register. Such alignment may avoid any abrupt edges in the outer profile of the sheaths, and facilitate insertion of the distal portion 14 into the anatomy (optionally through the introducer 19 and/or advancement through vasculature). However, after the stent-valve 10 has been released from the accommodation region 18, if the operator may desire to close the sheaths, there may be a tendency for the open ends 20b and 22b no longer to be closely aligned. Such misalignment may result in an abrupt edge in a case of confronting or slightly spaced open ends and/or difficulty of re-engaging the open ends in the case of trying to lap the open ends. It may be desirable to avoid an abrupt edge, especially at the open end 20b of the first sheath 20. When the catheter 12 is withdrawn after having released the stent-valve 10, the open end 20b may interfere with native tissue on the return path, or it may make it difficult to extract the distal portion through an introducer 19, especially if the distal portion 14 is a tight fit within the introducer 19. During such withdrawal, the second sheath 22 may be guided smoothly into the introducer 19 by the ramp surface 44 at the third tube coupling 44. However, an abrupt edge at the open end 20b of the first sheath 20 may obstruct smooth passage of the first sheath 20 for withdrawal through the introducer 19.

Alternatively, if the catheter 12 is withdrawn with one or both of the sheaths 20 and 22 in an open condition, an exposed abrupt edge (e.g. end face 92 in FIGS. 11-13) of the stent holder 24 may make it difficult to extract the distal portion through an introducer 19, especially if the distal portion 14 is a tight fit within the introducer 19. During such withdrawal, the second sheath 22 may be guided smoothly into the introducer 19 by the ramp surface 44 at the third tube coupling 44. However, the abrupt edge 92 of the stent holder 24 may obstruct smooth passage of the first sheath 20 for withdrawal through the introducer 19.

To address this, the distal portion 14 may comprise an interface member 50 (FIGS. 4 to 9). The interface member 50 may be deployable to:
(i) provide an interface at or between the generally confronting open ends 20b and 22b when (at least nearly) closed; and/or
(ii) align the open ends 20b and 22b to be substantially in register with each other and/or centred with respect to the catheter axis; and/or
(iii) define a bridge and/or a smooth profile between the confronting open ends 20b and 22b; and/or
(iv) provide an interface for the stent-holder 24 less abrupt than the exposed edge 92.

In some embodiments, the interface member 50 may be deployable as part of the sequence during or after release of the stent-valve 10.

In some embodiments, the interface member 50 may be translatable along the catheter axis from a non-deployed condition (FIG. 4) to a deployed condition (FIGS. 5 to 9). For example, the interface member 50 may be initially be stowed within one of the sheaths (for example the second sheath 22) in a non-deployed condition, and be translatable to or towards the open end of the sheath (22) to transition to its deployed condition. Stowing a movable interface member 50 initially within the second sheath 22 may avoid having to elongate the first sheath 20 unnecessarily to accommodate the interface member 50. As illustrated below, in some embodiments, the interface member 50 may be substantially freely translatable within a predetermined range of movement, and be configured to move with, or in response to, sheath movement. The interface member 50 may be referred to as a shuttle. The interface member 50 may be slidable (e.g. captively slidable) on one of the tubes 26, 28, 32, 38.

In some embodiments, the interface member 50 (or at least a portion 52 thereof) may be expandable. Transition from a non-deployed condition (FIG. 4) to a deployed condition (FIGS. 5 to 9) may include expansion of the expandable portion 52. For example, the expandable portion 52 of the interface member may be radially expandable. The expandable portion may be self-expandable from a compressed state.

In the illustrated embodiment, the interface member 50 may be both movable and self-expandable. Referring to FIG. 4, the interface member 50 may initially be stowed within one of the sheaths (for example the second sheath 22 as mentioned above) in a compressed non-deployed condition. The sheath 22 may constrain the interface member 50 in a compressed condition. The interface member 50 may be accommodated at one end of the accommodation region 18 where the interface member 50 may not interfere with the stent-valve 10.

As part of the release of the stent-valve 10 as explained above, the second sheath 22 may be retracted proximally. However, travel of the interface member 50 in the proximal direction may be restrained, for example, by the step profile of the first tube coupling 34. Retraction of the second sheath 22 may therefore cause relative movement between the second sheath 22 and the interface member 50, resulting in the interface member 50 transitioning towards the open end 22b of the sheath 22. When the interface member 50 may no longer be constrained by the sheath 22, the interface member 50 (or the portion 52) may self-expand. Upon expansion, the interface member 50 may become too large to be received again entirely within the sheath 22. The interface member 50 may at least partly "float" captive on the catheter between the stent holder 24 and the second sheath 22.

In some embodiments, it be may desired to re-close the sheaths 22 and 24 prior to removing the catheter 12 from the body. When the second sheath 22 is reclosed after release of the stent-valve 10, the interface member 50 may at least partly self-locate or "float" at the open end 22b. The interface member 50 may be pushed distally towards the stent holder 24 and/or the open end 20b of the first sheath. Optionally, the interface member 50 may be pushed distally until its travel is stopped by the stent holder 24 and/or the first sheath 20. For example, if the first sheath 20 is currently in its open position, the interface member 50 may advance until its travel is stopped by the stent holder 24. Thereafter, when the first sheath 20 is closed, the interface member 50 may cooperate with the open end 20b of the first sheath 20 as explained above.

Optionally, the interface member 50 may be dimensioned at one end, or both ends, to be partly insertable into a respective open end of a sheath even when the expandable portion 52 (for example, intermediate the ends) is expanded and is oversize with respect to the open ends of the sheaths. Such insertion can provide positive engagement and cooperation between the (or each) sheath and the inter-face member. Such insertion can also provide a degree of self-alignment or self-centring between the (or each) sheath and the interface member. If both ends of the shuttle insert into respective sheaths, the sheaths may also self-align or self-centre in register with each other.

Additionally or alternatively, the expandable portion 52 of the interface member 50 may have a generally smooth annular bulge, or bulb, shape. The expandable portion may have generally rounded or ramp surfaces at its opposite axial ends. Such a shape or shapes may provide a smooth transition between the interface member 50 and each open end 20b and 22b, and/or a generally smooth profile or bridge between the open ends 20b and 22b. The shape may further enhance self-alignment or self-centring of the open ends 20b and 22b in register with each other.

The expandable portion 52 may be dimensioned such that, in the expanded state of the expandable portion 52, at least one of the open ends 20*b* and 22*b* will not pass entirely over the expandable portion. For example, in the case of confronting open ends 20*b* and 22*b*, optionally neither open end 20*b* and 22*b* may pass entirely over the expandable portion 52. In the case of lapping open ends 20*b* and 22*b*, optionally one of the open ends may pass over the expandable portion 52.

The ends of the interface member may be generally asymmetric. In the illustrated form, the proximal end 62 may be formed as a cone. The cone shape may provide a mounting surface for an optional skirt 60 described below, and/or provide a nesting profile to fit the within the third tube coupling 44. The distal end 64 may be formed as a generally annular rim with a smooth, e.g. rounded, edge for guiding the open end 20*b* of the first sheath 20 as the first sheath 20 is closed thereover.

Referring to FIG. 21, in some embodiments, instead of closing the sheaths 20 and 22, it may be desired to remove the catheter 12 from the body while the distal portion 14 remains in an "open" condition. For example, at least the first sheath 20 may remain "open", whether or not the second sheath 22 is left "open" or is at least partly closed. In such case, the stent holder 24 and the interface member 50 may remain exposed at the distal portion 14. The interface member 50 may tend to slide towards the stent holder 24, either as a result of movement through the anatomy, or when the distal portion reaches the site of a closely fitting introducer 19. The interface member 50 may cooperate with the stent holder 24 to provide a more streamlined profile than the abrupt edge 92. In particular, the interface member 50 may comprise a conical surface 62 that defines a smooth ramp profile that will slide over the edge of an introducer 19 to guide the stent-holder 24 into the interior of the introducer and/or through the haemostasis valve. The interface member 50 may comprise an enlarged oversize portion 52 that acts as a stop to prevent the interface member 50 from passing through the introducer until the interface member 50 abuts or engages the stent holder 24. At that point, continued pulling to withdraw the catheter causes the enlarged portion 52 to collapse slightly, allowing the interface member 50 and stent holder 24 to pass smoothly through the introducer. The interface member 50 may optionally be configured to form a snug interference fit over the end of the stent holder 24 so that it remains in intimate contact with the stent holder 24.

The interface member 50 as described above may comprise any suitable materials, including one or more of: plastics, resiliently compressible plastics, metal and shape-memory alloys (e.g. nitinol). In the illustrated form, the interface member 50 comprises a generally non-compressible core member 54 carrying a shell 56 defining the expandable portion 52. The non-compressible core may, for example, be of plastics. The core member 54 may be longer than the shell 56, and define the end profiles 62 and 64 described above. The shell 56 may, for example, be of metal or shape-memory alloy (e.g. nitinol) to provide a well-defined expanded shape. The expandable portion 52 may comprise segments defining a cage-like bulge or bulb.

In addition to, or as an alternative to, any or all of the above constructional features, the interface member 50 may optionally comprise a flexible sleeve or skirt 60. The sleeve or skirt 60 may optionally be constructed as plural petals or segments of material that may overlap or not overlap, and collectively behave as a sleeve or skirt, and all references herein to a skirt are intended to refer also to such petals or segments. The skirt 60 may be deployable from a folded or collapsed state to an expanded state. The skirt 60 may be substantially self expanding. In the folded/collapsed state, the skirt 60 may be retained and/or restrained within one of the sheaths 20 and 22. In the expanded state once the skirt 60 has been released, the skirt 60 may be dimensioned to fit outside the open end 20*b*, 22*b* or at least one of the sheaths 20, 22, respectively. In particular, the skirt 60 may cover at least partly the open end 20*b* of the first sheath 20. The skirt 60 may be made of any suitable material, for example, flexible plastics. In one form, the skirt 60 may be cut from a shaped balloon member, for example, as used in a known balloon catheter. A balloon catheter may be used for valvuloplasty. Such a balloon may be molded in its expanded shape, and a skirt 60 cut from such a balloon may be self-biased towards the expanded shape, but also be flexible and easily foldable to a collapsed state. Such a balloon is also designed to be of thin material having atraumatic characteristics.

In the illustrated example, the skirt 60 may be bonded to be an integral part of the interface member 50. The skirt 60 may be bonded to the proximal cone 62. The cone 62 may provide a suitable divergent surface for supporting the natural shape of the skirt 60.

Instead of being slidable, the deployable interface member 50 and/or skirt 60 could be substantially stationary with respect to the stent holder 24. In one example described later, the deployable interface member 50 and/or skirt 60 may be mounted on the stent holder 24.

FIGS. 10*a-c* illustrate different examples of attachment element 68 of the stent-valve for engaging different examples of stent holder 24, as illustrated in FIGS. 11-13 and 22. The stent-valve may comprise at least one attachment element 68, optionally two or three attachment elements 68, optionally more. Generally, each attachment element 68 may be defined by an apex 74 or 76, joining first and second struts 70 and 72 that extend from an end of the stent-valve 10. The struts 70 and 72 may be members defining a lattice or skeletal stent structure of the stent-valve 10. In the case of a lattice, the cell associated with the struts 70 and 72 may project axially beyond neighbouring cells of the lattice.

In FIG. 10*a*, the struts 70 and 72 may extend generally linearly to meet at apex 74 defining a generally V-shape. In FIGS. 10*b* and 10*c*, the apex 76 is slightly different by incorporating a U-shape between the ends of the struts 70 and 72. The U-shape may be straight sided (e.g., FIG. 10*b*) or it may have curved sides (e.g. FIG. 10*c*).

Referring to FIG. 11, a two-piece stent holder construction is described. However, it will be appreciated that the stent holder may id desired by made as a one-piece item. A two-piece example construction of stent holder 24 may generally comprise first and second parts 78 and 80 assembled together. The first part 78 may comprise a hub 82 from which project a plurality of projections 84. The second part 80 may comprise a casing having a hollow interior for fitting around at least a portion of the hub 82 from which the projections 84 project, and defining interstices 86 for accommodating the locking projections 84 with a space or clearance 88 therearound. The casing may be forked to define the interstices. The edge 90 of each interstice 86 may optionally be rounded or chamfered. A two-part assembly may enable a complex shape of stent holder 24 to be formed reliably and cost effectively. It may also permit different materials to be used as appropriate (for example, the first part may be of metal for strength, and the second part may be of plastics). However, as already mentioned, the stent-holder 24 may be formed as unitary item instead of an assembly of plural parts.

The projections 84 may be configured for fitting within the interior of the apex 74 or 76 of each attachment element 68, when the stent-valve 10 is in its collapsed state. The engagement between the projection 84 and the apex 74/76 traps the attachment element (and hence the stent-valve 10) against axial movement, at least in an axial direction away from the stent holder 24.

The projection 84 may be referred to as a radial projection because it generally projects in a radial direction. In some embodiments, the projection, or an edge thereof, may be inclined towards the distal direction, by an angle of, for example, not more than about 20 degrees, optionally not more than about 10 degrees, optionally not more than about 5 degrees.

In the example of FIGS. 11 and 12, the projection 84 has an elongate blade or fin shape, suitable for fitting within the interior of apex 74 (FIG. 10a). Use of a fin or blade can enable the projection 84 to have a desirably thin shape, while remaining strong (especially in the axial, elongate direction). In addition to the projection 84 trapping the stent-valve 10 against axial movement away from the stent-holder, the shape of the interstice 86 cupping the apex 74, and/or engagement between an end face 92 of the stent holder 24 and neighbouring cell apexes of the stent, may restrain the stent-valve 10 against axial movement in the opposite direction. The stent-valve 10 may thereby be retained firmly in position until expansion of the stent-valve 10 may disengage the or each attachment element 68 from the stent-holder 24.

In the case of a self-expanding stent-valve 10, the attachment elements may disengage when the portion of the stent-valve 10 from which the attachment elements 68 extend, is uncovered by a sheath (for example, the first sheath 20). Upon expansion of the stent-valve 10, the struts 70 and 72 move apart to open the V-shape of the apex 74. As the V-shape opens, this enlarges the interior of the attachment element 68 to facilitate disengagement between the projection 84 and the apex 74. The chamfered edge 90 of the interstice 86 also acts as a ramp surface to "lift" radially the struts 70 and 72 out of the clearance 88 as the struts 70 and 72 expand circumferentially and bear against the edge 90. In case the attachment elements 68 may stick accidentally within the interstice 86, the attachment elements 68 may be freed by slight rotation and/or axial displacement of the catheter, to promote further riding against the edge 90.

In the example of FIGS. 13 and 22, the projections 84 are fingers or pins, suitable for fitting within the interior of apex 76 (FIGS. 10b/c). Each pin (FIG. 13) may have a larger thickness than an equivalent fin (FIG. 12). In a collapsed condition of the stent-valve 10 (FIG. 13), the struts 70 and 72 may lie closely adjacent each other at the attachment element 68, such that the arc of the U-shape portion 76 extends around a first angle more than 180 degrees to define a closed or near closed eyelet having an aperture larger than the spacing of the struts, to accommodate the pin 84. The U-shape may be referred to as a horseshoe U-shape. The eyelet aperture and space between the struts may together define a keyhole type shape. Alternatively, the struts 70 and 72 may bear against each other at the attachment element 68 to close the eyelet. Either arrangement can restrain the attachment element 68 in both axial directions, merely by engagement between the attachment element 68 and the projection 84. This may be advantageous by enabling a larger chamfer surface to be used at the edge 90 of the interstice 86 and/or at the end face 92 of the stent-holder. A chamfered end face 92 may be desirable to facilitate withdrawal of the stent holder 24 and first sheath 20 through the stent-valve 10 once implanted.

In the expanded (or functional or non-collapsed) condition of the stent-valve 10 the struts 70 and 72 may move apart, and the arc of the U-shape apex 76 may extend around a second angle that is less than the first angle, to at least partly open the eyelet. The second angle may be about 180 degrees or less.

For example, the apex may have a substantially straight-sided U-shape. In a similar manner to that described above, opening of the apex 86 may facilitate disengagement from the projection 84. The chamfered edge 90 of the interstice 86 also acts as a ramp surface to "lift" radially the struts 70 and 72 out of the clearance 88 as the struts 70 and 72 expand circumferentially and bear against the edge 90.

FIG. 22 shows a stent holder equivalent to FIG. 13, optionally for production as a single-piece item. All of the stent holders illustrated in FIGS. 11-13 and 22 illustrate the provision of at least one ramp surface extending partly around each projection, to define ramp surface portions circumferentially either side of the projection and axially (e.g. distally) to one side of the projection. The ramp surface portions are inclined outwardly away from the projections. The clearance around the projection is open to the other axial (proximal side) and/or open radially outwardly. The radial height of the projection 84 may be accommodated entirely or at least substantially within the profile of the stent holder body. The stent holder body may be a surface of revolution. One difference that may be noted between on the one hand the example of FIGS. 11 and 12, and on the other hand the examples of FIGS. 13 and 22, is that in the latter example, the ramp surface extends to the floor of the clearance or interstice around the projection 84. The ramp surface may generally be inclined at an angle of between about 20 and about 40 degrees, optionally around 30 or 35 degrees.

Referring to FIGS. 14 and 23, the stent-holder 24 may carry a skirt (or may also be referred to as sleeve) 94. The skirt 94 may optionally be constructed as plural petals or segments of material that collectively behave as a sleeve or skirt, and all references herein to a sleeve/skirt are intended to refer also to such petals or segments. The skirt 94 may be similar to the skirt 60 described above, and the same constructional details may be used. FIG. 23 illustrates one example structure in more detail. The skirt 94 may comprise a generally tubular sleeve section 94a and a plurality of cuts or slits 94b defining joined petals or segments 94c. The petals 94c may substantially cover the projections 84 and/or the radial recess therearound. The slits 94b may permit the petals 94c to fold or flex outwardly open. The slits 94b may be aligned generally with the projections 84 or the radial recesses therearound. Such positioning of the slits 94b can ensure that the petals 94c do not obstruct expansion and detachment of the attachment elements of the stent-valve. Outward flexing of the petals may automatically cause the slits 94b to open, to allow the attachment elements to expand through the open slits.

The skirt 94 may function to facilitate loading of the collapsed stent-valve 10 into especially the first sheath 20, prior to use of the delivery catheter 12. Loading may be achieved by first opening the first sheath 20 (arrow 20a), folding back or open the skirt 94 (or the petals 94c thereof), collapsing the stent-valve 10 such that the attachment elements 68 engage in the stent-holder 24, and then moving the first sheath 20 its closed position (arrow 20c) covering the distal portion of the stent-valve 10. The skirt 94 may return flat to cover, at least partly, the attachment elements 68. Covering the attachment elements 68 may avoid the apex 74 or 76 creating an abrupt edge that obstructs closing of the first sheath 10, if the attachment element 68 is not perfectly flush with the surface of the stent holder 24. Covering the attachment elements 68 may also avoid one of the attachment elements accidentally passing outside the open end 20b of the first sheath 20. It will be appreciated that, when the stent-valve 10 comprises plural attachment elements 68, it may be difficult to see whether all of the attachment elements 68 are engaged perfectly into the stent holder 24 during loading. Covering the attachment elements 68 with the skirt 94 may reduce this problem, and may compensate to guide the open end 20b of the first sheath 20 over the attachment elements 68 even if not perfectly positioned. The skirt 94 may also protect the open end of the first sleeve 20 from rubbing aggressively on the edge of outer skirt material of the stent-valve.

The skirt 94 on the stent holder may also find use in a delivery catheter 12 that has only a single sheath (not shown).

In the arrangement of FIG. 14, the skirt 94 may be distinct from the optional skirt 60 of the separate interface member 50. FIG. 15 may illustrate an alternative arrangement in which a single sleeve or skirt 94 may additionally perform the function of skirt 60 as an interface element.

Referring to FIG. 15, following release of the stent-valve 10, the skirt 94 may be directed with its open end facing distally, in order to cover the open end 20b of the first sheath 20. The skirt 94 may extend outside the first sheath 20. Within the terminology of an interface member, the skirt 94 may be in a deployed state when extending outside the first sheath 20. The second sheath 22 may be advanced distally towards the first sheath 20. The second sheath 22 may optionally be advanced distally beyond its normal closed position.

Additionally or alternatively to the skirt 94, it will be appreciated that other deployable interface elements may be provided on, or form part of, the stent holder 24, or be mounted on the stent holder support tube. This would illustrate a further example of a deployable interface element that is not freely slidable within the accommodation region 18.

FIG. 16 illustrates a handle 100 for the proximal portion 16 of the delivery catheter, for controlling the distal portion 14 via the tubes 26-30 extending between the proximal and distal portions of the delivery catheter. The tubes 26 may optionally include or be connected to respective rigid portions that extend through the handle 100.

The handle 100 may comprise a fixed body 102 which extends substantially the length of the handle 100, and may have an elongate slot 104 through which control pins can slide, as described herein after. A fixing 106 may fixedly couple the body 102 to the first tube 26, such that the body 102 may control the relative position of the first tube 26. A grippable "first tube" handle 108 may be coupled to the body 102, for example, at the distal end of the handle 100.

The handle 100 may further comprise a "second tube" handle 110 having a helical guide 112 associated therewith. The helical guide 112 may optionally be formed in a separate component 112a that is coupled to rotate with the "second tube" handle 110. A slider 114 coupled to the second tube 28 may have a pin 116 that extends through the slot 104 into engagement with the helical guide 112. The "second tube" handle 110 may be rotatable about the body 102. Rotation of the "second tube" handle 110 (relative to the body 102) rotates the helical guide 112, causing the pin 116 and hence the slider 114 to move axially. The slider 114 transmits the axial movement to translate the second tube 28 relative to the first tube 26, thereby to translate the first (distal) sheath 20 with respect to the stent holder 24.

The handle 100 may further comprise a "third tube" handle 118 having a helical guide 120 associated therewith. The helical guide 120 may optionally be formed in a separate component 120a that is coupled to rotate with the "third tube" handle 118. A slider 122 coupled to the third tube 30 may have a pin 124 that extends through the slot 104 into engagement with the helical guide 120. The "third tube" handle 118 may be rotatable about the body 102. Rotation of the "third tube" handle 118 (relative to the body 102) rotates the helical guide 120, causing the pin 124 and hence the slider 122 to move axially. The slider 122 transmits the axial movement to translate the third tube 30 relative to the first tube 26, thereby to translate the second (proximal) sheath 22 with respect to the stent holder 24.

Optionally, the handle 100 may comprises at least one flushing port 126 through which liquid (e.g. saline) may be injected, in order to flush air from spaces that are open to the anatomy. In particular, it may be desired to flush the space between the first and second tubes, and the space between the second and third tubes. In some embodiments, a single or common flushing port 126 may be provided for flushing both spaces. A communication port or aperture (the position of which is indicated schematically at 128 and referred to hereinafter by the same numeral) may be provided for allowing liquid in one space to enter the other. For example, the flushing port 126 may be configured to admit liquid into the space between the first and second tubes. A communication port 128 in the second tube may permit the liquid also to enter the space between the second and third tubes. The communication port 128 is optionally positioned at the handle 100, or at least closer to the proximal portion of the catheter than to the distal portion, in order to flush the spaces thoroughly to the distal portion. Provision of a single or common flushing port 126 for flushing plural spaces may be advantageous in simplifying the number of connections and operations that an operator has to perform when preparing the catheter for use. Alternatively, if it is desirable to have independent control over flushing of each space, plural flushing ports 128 may be provided, each communicating individually with a respective space to be flushed.

The handle 100 may be configured to apply pre-tension to one or more of the tubes, as described above. Various mechanisms for applying pre-tension are envisaged. The mechanism may be part of the "second tube" handle 110, or it may be a separate mechanism capable of applying tension. In a simple, yet effective and intuitive form, the "second tube" handle 110 may be rotatable to generate pre-tension, and may be lockable in the tensioning position. The handle may be lockable using any suitable locks, such as a removable pin, or a ratchet mechanism. Additionally, the handle 100 may include an indicator ring for indicating the amount of rotation of the handle 110 to generate a desired amount of pre-tension. The indicator ring may be manually settable such that a first marker is in register with a counter-marker on the handle 110 when the first sheath is in a closed position without pre-tension. Once set, the indicator ring may indicate, by a second marker, the degree of further rotation by which the handle 110 should be turned or displaced to generate the pre-tension. The lock for locking the handle 110 in position, and/or the settable indicator ring, are generally indicated schematically at 110a. However, it will be appreciated that the lock and indicator ring may be separated and/or placed at different positions on the handle 100 as desired.

FIG. 20 illustrates a liner sleeve 150 that may be used with the catheter 12. The liner sleeve 150 may act as a friction reducing liner between the catheter 12 and an introducer 19 (for example, a standard arterial introducer) through which the catheter is inserted into the body. The liner sleeve 150 may reduce friction on the catheter tubes, especially the outer tube 30, permitting easier deployment of the stent 10. A standard arterial introducer includes a haemostasis valve 19a for preventing blood reflux and air aspiration. The haemostasis valve 19a may be a quite aggressive multiple flap valve in order to function with a wide range of different equipment types and sizes that could be introduced into the artery. The aggressiveness of the haemostasis valve may tend to obstruct fine displacement of the tubes of the delivery catheter 12 for controlling translation of the sheaths at the distal portion. The liner sleeve 150 provides a low friction interface between the third tube 30 and the introducer 19. The liner sleeve 150 may be captive on the catheter 12, and slidable axially along the catheter length. The liner sleeve 150 may include, at its proximal end, a stop 152 that limits the extent of entry into the introducer. Additionally or alternatively, the liner sleeve 150 may include a portion 154 for removable interference fit with a socket 156 of the handle 100. This permits the liner sleeve 150 to be stowed connected to the socket 156 of the handle 100, and separated from the handle 100 when desired to advance the liner sleeve 150 into operative position within an introducer 19. The liner sleeve 150 may optionally additionally comprise a seal 158 for effecting a substantially blood-tight seal between the liner sleeve 150 and the outer tube 30 of the catheter 12. The seal 158 may be configured uniquely for the dimension of the catheter 12, and so may be substantially less aggressive than the haemostasis seal 19a of the introducer 19. For example, the seal 158 may be formed by an O-ring. The seal 158 may optionally be provided at the stop 152 or the connector 154, such that the seal 158 is not subjected to the forces within the introducer 19. Alternatively, the seal 158 may be positioned elsewhere along the length of the liner sleeve 150.

When deployed into the introducer, the liner sleeve 150 may not be fixed axially and/or rotationally with respect to the remainder of the catheter 12, allowing the catheter to be manipulated without obstruction. In some embodiments, the length of the liner sleeve 150 projecting distally from the stop 152 may be not be greater than about 30 cm, optionally not greater than about 25 cm, optionally not greater than about 20 cm, optionally not greater than about 15 cm, optionally not greater than about 10 cm.

FIG. 24 illustrates a modification of the delivery catheter including a ball joint (the terms ball joint, ball socket, ball socket articulation, and ball socket connection are all interchangeable) in at least one tubular member of the catheter. The ball joint may be provided just proximal to the stent accommodation region (also referred to herein as stent-holding region or compartment) of the catheter, such that the ball joint can provide a high-flexibility region just proximal to the stent-holding compartment. The ball joint can be within 5 cm proximal of the stent holding compartment. The ball joint can also be 0.1, 0.5, 1, 2, 3, 4 or 4.5 cm proximal of the stent holding compartment. The ball joint can also be between 1 and 2 cm proximal of the stent holding compartment. The ball joint may be provided in a tubular member of the catheter that moves axially with respect to the position of the stent. That is, the tubular member, according to so-me embodiments, can be moved in a proximal 22A or distal 20A direction (also as shown in FIG. 1) to release the stent. In this case, the distance measurement above is defined to be when the tubular member is in a position corresponding to a closed position, e.g. a most closed position for that tubular member. An example of this closed position is shown in FIG. 24. In the closed position, the sheaths may meet end to end, or remain spaced from each other.

The ball joint may be provided in the outer tubular member of the catheter assembly. The ball joint is preferably hollow or includes an aperture to permit passage of one or more inner tubular members. In some embodiments, there is a single inner tubular member that passes through the outer tubular member. This inner tubular member can be a guide-wire receiving lumen. Also a stent holder can be mounted on this inner tubular member. There can also be at least two tubular members that pass through the outer tubular member. These two or more inner tubular members can be arranged one within the other. There can also be three, four, five, six, seven, eight, nine or ten inner tubular members. Each of these can be nested within each other.

In some embodiments, the ball joint can allow bending of the tubular members through a range of up to at least 45°, compared to the straight-axis of the catheter at that point. The ball joint can also allow bending of the tubular members of up to at least 40°, compared to the straight-axis of the catheter at that point. The ball joint can also allow bending of the tubular members of up to at least 30°, compared to the straight-axis of the catheter at that point. The ball joint can also allow bending of the tubular members of up to at least 20°, compared to the straight-axis of the catheter at that point. The ball joint can also allow bending of the tubular members through 20°, 21°, 22°, 23°, 24°, 25°, 26°, 27°, 28°, 29°, 31°, 32°, 33°, 34°, 35°, 36°, 37°, 38°, 39°, 41°, 42°, 43° and 44°, compared to the straight-axis of the catheter at that point. Such high flexibility would be difficult to achieve with a continuous bending member of equivalent cross-section diameter, without risk of kinking the continuous member.

In some embodiments, the ball joint has a transverse outer diameter (e.g., measured in a cross-section direction to the axis of the catheter) that is not greater than a diameter of at least one adjacent tubular member of the catheter assembly. This enables the ball-joint to be accommodated without enlarging the size profile of the catheter assembly. The profile of the tubular member adjacent to the ball joint may blend smoothly into the profile of the ball joint, to define a generally smooth continuous surface, even when the catheter assembly is flexed at the ball joint. If desired, the transverse outer diameter of the ball joint may be larger than the a diameter of both adjacent tubular members of the catheter assembly leading to the ball joint.

In some embodiments, the transverse outer diameter of the ball joint is not greater than a largest tubular member diameter of the catheter assembly. For example, for a catheter assembly insertable into the body using an introducer of 18 French size, the maximum diameter of an outer tubular member is approximately 6 mm (not greater than 7 mm). The transverse outer diameter of the ball joint might then be no larger than this maximum diameter. In some embodiments, the length of the ball joint (in an axial direction of the catheter assembly) may be up to about two thirds of the transverse outer diameter of the ball joint.

In some embodiments, the ball joint can also allow an axial force to be applied along the length of the tubular members, for pushing forward (distally) or drawing back (proximally) the tubular members. For example, the outer tubular member may comprise a sheath (e.g. proximal sheath part) that at least partly encompasses the stent, and the sheath may translate axially forwards or backwards under the axial force to shift from a closed state to an open state. The axial force may be applied through the ball joint. The ball joint can thus form part of a portion or sub-assembly of the catheter that moves axially with regards to the stent position on the catheter.

In some embodiments, the ball joint can also allow relative rotation between the two parts of the tubular members on either side of the ball joint. The relative rotation may be limited up to one turn, or in some embodiments, the relative rotation may also be limited up to two, three, four, five, six, seven, eight, nine or ten turns. Alternatively, it may be unlimited. Either arrangement may enable the stent-holding compartment of the catheter to be rotated, while the outer body of the catheter remains stationary in the artery without rotation. The outer body of the catheter can act like a bushing within which the other tubular members turn, without friction with regards to the artery wall. The torsion can be applied via the other (one or more) tubular members carried within the catheter and passing through the ball joint to the distal section of the delivery device (at least distal of the ball joint). Alternatively, a hydraulic or electronic actuator may generate rotary movement at the distal part (stent-holding compartment) in response to a suitable fluid/electronic signal supplied via a electronic signal line or a fluid conduit.

FIG. 24 presents an example of a stent delivery device with a ball joint according to some embodiments of the present disclosure. As shown, ball joint 1 is provided in the outer tubular member 30 of the catheter, which is the tubular member for drawing back (proximally 22A towards the catheter handle) the proximal outer sheath (second sheath) 22 that covers (at least) a portion of the stent 10. For pulling back the proximal sheath, an axial force is applied from a handle along the catheter length, and then through the ball joint to the outer sheath. Rotation is achieved by applying a torsional force to inner tubular members 26 and/or 28 within the catheter. These turn the stent from within. The stent holder 30 transmits the torsional force from the other interior tubular members to rotate the stent about the catheter axis. The friction between the stent and the outer sheath also turns the outer sheath. The ball joint enables the outer sheath to turn freely without torsion being applied to (or resisted) by the body of the catheter. FIG. 1 also shows that the stent holder can be located distally 6A or proximally 6B. The stentholding compartment is made up of the proximal sheath 22 and the distal sheath 20. The distal sheath is attached to the inner tubular members. When the inner tubular members are extended distally, the distal sheath can also be pushed distally and off of the stent. Likewise, the proximal sheath can be pulled proximally, as described above. The inner most tubular member also forms a guidewire lumen 3 that extends through the center of the catheter.

The ball joint and the portions of the tubular member coupled thereto may be of any suitable material, e.g. metal (e.g. stainless steel) or plastics (e.g. nylon).

The socket part of the ball joint may communicate with a stepped-down, or even necked-down, region of the tubular member, in order to allow the spherical extent of the socket surface to be increased.

A related aspect may be to provide a high-flexibility portion of the catheter adjacent to the stent-holding compartment. The high-flexibility may be defined as having a bending resistance less than 50% of the tubular member on either side of the high-flexibility region. The high flexibility region may also have a resistance of 10%, 15%, 20%, 25%, 30%, 35%, 40% or 45% of the tubular member on either side of the high-flexibility region. The high-flexibility region may have an axial length of less than 5 cm. The high-flexibility region may also have an axial length of between 1 and 2 cm. One implementation for the high-flexibility region may be using a ball joint as above. Another may be to use a segment of high-flexibility tubing joined to (or integral with) the catheter tubing.

The flexing and rotary articulation of a ball joint may even be separated into two separate connections, joints or couplings, provided that both of these are close to the stent-holding compartment of the catheter. The two couplings are generally not more than 5 cm apart. The two couplings can also be between 1 and 2 cm apart. The flexing connection can be positioned closer to the stent-holding compartment to compensate for the rigidity of the adjacent stent, but the order could easily be reversed according to a particular implementation.

It will be appreciated that including a ball joint in the outer tube may restrict the amount of torque transmittable through the outer tube. The construction of other inner tubes may optionally be modified to transmit torque, for example, using the principles described previously.

FIGS. 17, 18 and 19 illustrate a detailed example of a stent-valve 10 for which the delivery catheter 12 of any of the preceding embodiments may be eminently suitable. The stent-valve 10 may be of a self-expanding type that is resiliently biased towards the expanded and/or functional state, and is compressible to a compressed state by application of suitable radial compression forces. The stent-valve 10 remains in its compressed state while constrained. When the constraint is removed, the stent-valve 10 self expands towards the expanded and/or functional state. Alternatively, the stent-valve 10 may be of a non-self-expanding type that requires application of an expansion force to transform the stent-valve 10 from the compressed state 10' to the expanded state.

The stent-valve 10 may comprise a stent component 134 supporting a plurality of valve leaflets 136. The leaflets 136 may collectively be referred to as a valve component, whether or not the leaflets 136 form an integral unit. The stent component 134 may provide an anchoring function for anchoring the stent-valve in the native anatomy and/or a support function for supporting the valve leaflets 136. The stent component 134 may be of any suitable material or materials. The stent component 14 may be of metal. Example materials include shape memory and/or superelastic alloys (for example, nitinol), stainless steel, or cobalt-chromium alloy. In the illustrated form, the stent component 134 is self-expanding and is of shape memory/superelastic alloy (e.g. nitinol). However, the stent component 134 could also be substantially non-self expanding.

The stent component 134 may have any profile desired for anchoring and/or aligning the stent-valve 10 with respect to the native anatomy at the desired implantation site. In some embodiments, the stent component 134 may be generally cylindrical in shape, or comprise one more generally cylindrical portions or portions lying on a generally cylindrical surface (e.g. 140c and 142a). Additionally or alternatively, the stent component 134 may be generally non-cylindrical in shape or comprise one or more generally non-cylindrical portions or portions lying on a non-cylindrical surface (e.g. 140a, 140b, and 144). Additionally or alternatively, the stent component 134 may comprise one or more anchor projections, and/or one or more stabilization portions.

Viewed in one aspect, the stent component 134 optionally has an inflow end and an outflow end, optionally is self-expandable from a compressed state for delivery towards a functional state upon implantation, the stent component 134 comprising an outflow structure, for example, in the form of a plurality of arches 144a at the outflow end each having an apex at the outflow end, the stent component further comprising a crown (e.g. superior crown) 140b intermediate the inflow and outflow ends, the crown 140b having a free extremity intermediate the inflow and outflow ends and directed towards the outflow end, and the stent-component further comprising a fixation section (e.g. inferior crown) 140a between the crown and the inflow end.

Additionally or alternatively, the stent component 134 optionally comprises an anchoring portion 140 defined, for example, by an inferior crown 140a and a superior crown (or other fixation section) 140b that together define a groove and/or waist 140c therebetween. The anchoring portion 140 may have a first resistance to compression, and may comprise a cellular lattice.

The stent component 134 optionally (further) comprises a valve support portion 142 comprising, for example, a plurality (e.g. three) commissural support posts 142a. The commissural support posts 142a may be arranged on a pitch circle diameter smaller than an extremity of at least one of the crowns 140a and 140b. The commissural support posts 142a may be arranged on a pitch circle diameter corresponding to the waist 140c. The commissural support posts 142a may partly overlap at least one of the crowns 140 and 142 in the axial direction, and extend axially beyond that respective crown. The commissural support posts 142a may be framelike. The commissural support posts 142a may have a shape that follows, at least approximately, a peripheral contour of the valve, at least in the region of the valve periphery adjacent to the commissural support posts.

The stent component 134 optionally (further) comprises a stabilization or alignment portion 144 which may represent an outflow structure. The portion 144 may be defined, for example, by a plurality (e.g. three) wings or arches 144a. The arches 144a may extend from tips of the commissural support posts 142a, to define a vaulted structure thereover. The alignment portion 144 may have a greater flexibility than the anchoring portion 140 and/or the valve support portion 142. The alignment portion 144 may have a second resistance to compression that is smaller than the first resistance to compression of the anchoring portion 140. The alignment portion 144 may be less rigid (e.g. radially) than the anchoring portion 140 and/or the valve support portion 142.

The stent component 134 optionally (further) comprises an attachment element 68 for attaching the stent component 134 to a stent holder 24 of the delivery catheter 12. In the present embodiment, the attachment portion 68 is defined by a plurality (e.g. three) of extensions of cells of the inferior crown 140a, and have a shape corresponding to one of the examples of FIGS. 10a-c.

The valve component or leaflets 136 may be of any suitable natural and/or synthetic material(s). For example, the valve component/leaflets 136 may comprise porcine and/or bovine pericardium and/or harvested natural valve material. The leaflets may be supported to coapt or collapse to a closed position to obstruct flow in one direction therepast, while flexing apart to an open position to allow flow in an opposite direction. The valve component/leaflets 136 may be accommodated at the valve support portion 142 and/or at least partly within the anchoring portion 140. The leaflets may have side tabs. The tabs of adjacent pairs of leaflets may pass in pairs through slots in the support posts 142, be folded back and sutured on either side of the slot. The support posts 142a may have lines of suture holes either side of the slot to accommodate the sutures. Further suture holes may be provided above and/or below the slots. If desired the suture hole above the slot (indicated at A in FIG. 19) and/or the suture hole below the slot, may be omitted to save space.

The stent-valve 10 (e.g. the valve component 136) may further comprise an inner skirt and/or an outer skirt covering at least partly a respective inner or outer surface portion of the stent component 14. For example, the skirt(s) may cover at least a portion of the anchoring portion 140 and/or at least a portion of the valve support portion 142. The skirt(s) may be made of any suitable material, including PET and/or pericardium. The pericardium may be of the same material as the leaflets. In some embodiments, the inner and outer skirts may partly overlap each other in a skirt overlap region A in FIG. 17, and include non-overlapping portions extending axially above and below, respectively, the overlap region A. The inner skirt may be advantageous in channel blood towards the leaflets and preventing leakage of blood through the interstices of the lattice structure. The outer skirt may be advantageous in preventing leakage of blood at the interface between the stent-valve and surrounding tissue. Providing both skirts, but with only partial overlap, may enable the advantages of both to be obtained, but also reducing full overlap of material (which would otherwise increase the thickness of material of the stent-valve, making it more difficult to compress the stent-valve to a small size). The partial overlap nevertheless enables a reliable seal to be achieved between the inner and outer skirts.

In use, viewed in one general aspect, at least a portion of the inferior crown (or other fixation section) 140a may be received and constrained by the first sheath 20. At least a portion of the stent-component 134 not covered by the first sheath 20 may be received and constrained by the second sheath 22. As explained earlier and described in more detail below, a method of releasing the stent-valve 10 may include moving the second sheath 20 to an open position in order to deploy the crown/superior crown 140b, followed by the support section 142, and finally the arches 144a. For example, these elements may be deployed on an aorta side of a native and/or failed valve. Thereafter, once the operator is satisfied with the position and/or function of the stent-valve 10 within the native anatomy, the first sheath 10 may be moved to its open position in order to deploy the inferior crown 140a. Simultaneously, the attachment elements 68 may release from the stent-holder 24.

Such a deployment sequence is different from that described in the aforementioned WO-A-2009/053497 and WO-A-2011/051043. Nevertheless, it has been appreciated that deploying the arches 144a after the crown 140b is still highly effective in permitting the arches to function. Notably, the arches may be deployed prior to uncovering of the fixation section 140a for deployment.

In some embodiments, the arches may be configured for aligning the stent-valve with respect to an axis of the ascending aorta by contact with a wall of the ascending aorta. For example, the arches may be bendable independently of each other. The crown may be configured for engaging and/or seating against existing leaflets from an outflow side. The fixation section may be configured for engaging an existing annulus.

Deploying the arches before the fixation section may permit self-alignment of the stent-valve by the action of the arches, before the fixation section deploys to anchor the stent-valve at the annulus of the existing valve.

There now follows a detailed description of how the apparatus described above may be used in one example. The description may be modified according to which features of the apparatus may be implemented according to the actual embodiment used. The order of the individual steps may be changed as desired. The steps are grouped by topic. The order of the topics may be changed as desired. The order of steps within each topic may be changed as desired. The following description may focus principally on features of the delivery catheter previously described; additional steps not described here may be included as part of the procedure, as may be known to practitioners in the field of transcatheter stent-valve implantation.

A: Loading of the stent-valve into the accommodation region:

A1: The first and second sheaths 20 and 22 are each translated open by using the controls 110 and 118 of the handle 100. The petals 94c of the skirt 94 are folded back to expose the projections 84 of the stent holder.

A2: The stent-valve 10 is compressed in place in the accommodation regions. A conventional crimper may be used. The stent-valve is arranged with its end (for example, inflow end) having the attachment elements positioned distally in the accommodation region, and in register with the projections 84. The fixation section/inferior crown 140a may be compressed first, such that the attachment elements 68 mate with the projections 84. Using the handle 110, the first sheath 20 may be translated proximally to at least partly cover the fixation section/inferior crown 140a, and capture the stent-valve by its attachment elements. During such translation, the petals 94 may unfold flat to lie between the interior surface of the first sheath 20, and an exterior surface portion of the stent-valve. Next the remaining sections of the stent-valve may be compressed (e.g. the crown/superior crown 140b; the valve support section; and the arches) and the second sheath 22 is translated distally to at least partly cover the stent-valve from the arches to the crown/superior crown 140b to constrain these sections of the stent-valve compressed. As mentioned previously, in the closed positions of the first and second sheaths, the ends of the sheaths may meet substantially end to end, or the sheaths may remain spaced apart.

B: Preparation of the delivery catheter for introduction into the body (following steps A):

B1: The delivery catheter may be flushed by injecting liquid (e.g. saline) via the at least one flushing port 126. Optionally, plural spaces within the delivery catheter may be flushed by injecting liquid through a single and/or common port 126.

B2: The first tube 26 may be pre-tensioned by rotating the second tube handle 110 to "overclose" the first sheath. The amount of pre-tension to apply may be indicated by manually setting the indicator ring such that a first marker on the indicator ring aligns with a counter-marker on the handle 100. The second tube handle 110 is further rotated manually by an amount indicated by a second marker on the ring to generate the pre-tension. The second tube handle 100 may optionally be locked in the pre-tensioning position, in order to avoid the handle slipping in use and relaxing the pre-tension before the moment intended.

C: Steps carried out on the patient prior to implantation (following steps A or B):

C1: An arterial introducer 19 is placed to penetrate percutaneously an artery, for example, the femoral artery or the subclavian artery. A guide wire is introduced through the introducer 19 and navigated along the vasculature to traverse the valve to be replaced, for example, an aortic valve.

C2: A balloon catheter may optionally be introduced through the introducer 19 and advanced along the guide wire to the valve to be replaced. Valvuloplasty may be performed to free the valve leaflets in the case of a stenosed valve. The balloon catheter is then removed.

D: Stent-Valve Implantation (following steps A, B and C):

D1: The delivery catheter may be fed over the guidewire towards the introducer 19, with the guidewire being received within the lumen of the first tube 26. The distal portion of the delivery catheter may be introduced through the introducer. Thereafter the delivery catheter may be fed progressively through the introducer, to advance the distal portion along the guidewire to the location of the valve to be replaced.

D2: At some stage, at least after the distal portion has passed through the introducer 19, the liner sleeve 150 may be separated from the handle 100, and slid distally along the catheter stem and into the introducer 19 to provide a reduced friction fit in the introducer. This may permit easier advancement of the catheter through the vasculature, and/or easy manipulation of the sheaths at the following steps.

D3: When the distal portion is approximately in position, or slightly high in the ascending aorta, the operator may, if desired, rotate the delivery catheter, to rotationally align the stent-valve with the native anatomy. Although the geometry of the stent-valve itself may not require such rotational alignment, some practitioners may prefer the possibility to align the stent-valve with the native valve, such that the stent-valve can replicate the natural valve function as closely as possible. As described previously, the combination of the braided tubes 26 and 30, and/or the braid characteristic of the third tube 30, permits good transmission of torque from the handle 100 to the distal portion, despite the relatively long length of the delivery catheter. The rotational orientation of the stent-valve may be observed using suitable imaging equipment, for example, X-ray imaging equipment.

D4: With the distal portion still approximately in position, or slightly high in the ascending aorta, the third tube handle 118 may be operated to translate the second sheath 22 proximally, and release the sections of the stent-valve previously covered by the second sheath 22. This may include the crown/superior crown 140b, the arches 144a, and any stent sections in between (e.g. the support section 142). The translation of the second sheath 22 may release first the crown/superior crown 140b, followed last by the arches 144a. If pre-tension is used in step B2, the pre-tension may bias the first sheath proximally preventing any tendency for the first sheath to creep distally as a result of the reaction forces applied though the tubes during the manipulation of the second sheath. It may be appreciated that although the pre-tensioning step is described as part of the preparation at step B2, the application of pre-tension may be performed later at any stage before D4, even after the catheter has been advanced to the valve to be replaced. Performing the pre-tensioning step later may, in some cases, improve the flexibility of the catheter for tracking along the guidewire. Additionally or alternatively, it may be appreciated that if the liner sleeve 150 if used at step D2, the liner sleeve 150 may reduces frictional resistance against movement of the third tube 30 within the introducer 19, thereby making the operation of translating the second sheath 22 easier and smoother.

D5: The operator may push the catheter gently until the deployed crown/superior crown 140b bears against the existing leaflets of the valve to be replaced. Upon such placement, the operator may feel resistance, and effectively feel that the crown/superior crown 140b is seated correctly against the leaflets. Additionally or alternatively, the position may be monitored by suitable imaging equipment, such as X-ray imaging equipment. During such manipulation of the catheter with the stent-valve partly deployed, the engagement between the stent holder 24 and the attachment elements 68 keeps the stent-valve firmly anchored to the delivery catheter.

D6: When the operator is satisfied about the position of the crown/superior crown 140b, the operator may operate the second tube handle 110 to translate the first sheath 20 distally in order to release the fixation section/inferior crown 140a. If the second tube handle 110 has been locked in position as part of the pre-tensioning operation, the lock may be removed or disengaged to allow the pre-tension to be relaxed, and the second tube instead to apply a compression force for translating the first sheath distally. As mentioned previously, the construction of the second tube 28 provides good column strength for transmitting the compression force from the handle 100 to the first sheath 20.

D7: Upon removal of the first sheath 20, the fixation section/inferior crown 140a deploys to anchor the stent-valve in position. The attachment elements 68 expand radially outwardly and may expand circumferentially, to release automatically from the projections 84 of the stent holder 24. The ramp surfaces at least partly surrounding the projections 84 lift the expanding attachment elements radially clear of the stent holder 24. In the unlikely event that any attachment element 68 may remain engaged to the stent holder 24, the ramp surfaces also provide a facility to free the attachment elements by slight axial and/or rotational movement of the delivery catheter, which encourages the attachment element to ride against a ramp surface.

D8: Following release of the stent-valve 10 from the accommodation region, a first step of removal of the delivery catheter may be to withdraw the portion of the delivery catheter that is distal of the valve leaflets 136, through the valve leaflets to the proximal side (e.g. into the ascending aorta). Thereafter the, the delivery catheter may be withdrawn with the sheaths 20 and 22 open or closed.

It may be appreciated that the

E: Removal of delivery catheter while open (after step D):

E1: The delivery catheter may be withdrawn without any further manipulation or translation to close the sheaths 20 and 22. If the interface member 50 has not already been deployed from the second sheath 22, the second sheath 22 may be further translated open (proximally) to release and deploy the interface member 50.

E2: The delivery catheter may be withdrawn by pulling proximally through the introducer 19. The liner sleeve 150, if used, may remain in place at the introducer, as the stem is pulled through, or the liner sleeve 150 may manually withdrawn or may self-withdraw as a result of friction.

E3: As the distal portion of the delivery catheter approaches the introducer, the second sheath 22 may pass smoothly into the introducer, by virtue of the streamlined shape of the third tube coupling 44. The interface member 50 may translate distally to abut the stent holder 24, either by virtue of the movement of the catheter in the blood stream, or by contact between the interface member 50 and the end of the introducer 19. As explained previously, the interface member 50 has a shape that presents a streamlined profile to guide the distal portion, with the stent holder 24, smoothly into the introducer. The distal portion may thus be withdrawn through the introducer even when the sheaths are open. The inter-face member 50 remains deployed during the withdrawal.

F: Removal of the delivery catheter with sheaths closed (after step D, and instead of step E):

F1: If the interface member 50 has not already been deployed from the second sheath 22, the second sheath 22 may be further translated open (proximally) to release and deploy the interface member 50.

F2: The first and second sheaths may be translated towards a closed state, with the first sheath being translated proximally, and the second sheath being translated distally. As explained previously, the interface member 50 has a shape that may provide a bridge or interface between the ends of the two sheaths to define a smooth profile without abrupt edges. The distal portion may thus be withdrawn smoothly through the introducer. The interface member 50 remains deployed during the withdrawal.

F3: The liner sleeve 150, if used, may remain in place at the introducer, as the stem is pulled through, or the liner sleeve 150 may manually withdrawn or may self-withdraw as a result of friction.

It will be appreciated that the foregoing description is merely illustrative of preferred forms of the invention, and that many modifications, equivalents and improvements may be used within the scope of the invention.

The invention claimed is:

1. A transcatheter aortic valve implantation system, comprising:
    an aortic stent-valve comprising a stent component and valve leaflets supported by the stent component, the stent component having an inflow end and an outflow end and being self-expandable from a compressed condition for delivery towards an expanded functional condition, the stent component comprising outflow structure at the outflow end, a crown intermediate the inflow and outflow ends, the crown having a free extremity intermediate the inflow and outflow ends and directed towards the outflow end, and the stent-component further comprising a fixation section between the crown and the inflow end;
    a delivery catheter having a distal portion insertable into the anatomy, the distal portion comprising a stent-valve accommodation region for accommodating the stent-valve in the compressed condition for delivery, a first sheath for covering at least a portion of the fixation section at the accommodation region to constrain the fixation section compressed, and a second sheath for covering at least a portion of the outflow structure and at least a portion of the crown at the accommodation region to constrain the outflow structure and the crown compressed, the second sheath being translatable in a proximal direction to uncover the crown and the outflow structure for deployment, and the first sheath being translatable in a distal direction to uncover the fixation section for deployment;
    wherein in a condition in which the stent-valve is loaded at the accommodation region and the system is ready for introduction into the anatomy, the first and second sheaths are spaced apart from each other in an axial direction such that a portion of the stent-valve is not covered by either sheath.

2. The system of claim 1, wherein the outflow structure comprises a plurality of arches having apexes at the outflow end of the stent component.

3. The system of claim 1, wherein translation of the second sheath deploys the crown followed by the stabilization arches to permit axial seating of the crown against native leaflets and generation of axial alignment forces by the arches contacting the ascending aorta, and translation of the first sheath deploys the fixation section to anchor the stent-valve.

4. The system of claim 1, wherein the stent-valve is configured such that, when the first sheath covers at least a portion of the fixation section, and the second sheath is translated proximally to uncover the crown and the outflow structure, the stent component defines a partly deployed substantially flared shape from the portion of the fixation section constrained by the first sheath, towards the free extremity of the crown, the flared shape permitting universal seating of the crown against native leaflets.

5. The system of claim 4, wherein the partly deployed substantially flared shape corresponds to the crown being partly deployed in a form smaller than its fully deployed shape.

6. The system of claim 1, wherein the stent-valve further comprises an inner skirt covering a portion of an inner surface of the stent component, and an outer skirt covering a portion of an exterior surface of the stent component, the inner skirts including a region of partial overlap, and wherein the space between the first and second spaced apart sheaths is in register with at least a portion of the region of partial overlap of the inner and outer skirts.

7. The system of claim 1, configured for transvascular delivery of the stent-valve to the heart.

8. The system of claim 1, wherein the first sheath is shorter than the second sheath.

9. The system of claim 1, wherein the first sheath and the second sheath are non-overlapping and/or have a same diameter as each other.

10. The system of claim 1, wherein the delivery catheter further comprises an interface member at the accommodation region, the interface member being deployable upon translation of at least one of the sheaths, the interface member providing a guide surface for aiding withdrawal of the delivery catheter from the anatomy after the stent valve is deployed.

11. The system of claim 1, wherein the delivery catheter comprises a flexible stem portion extending between the distal portion and a control handle at a proximal portion of the delivery catheter, the stem portion comprising a plurality of flexible slidable tubes nested one within another for controlling translation of the sheaths in response to operation of the control handle, wherein the control handle comprises an actuator for applying pre-tension to at least one of the tubes for biasing the first sheath in a proximal direction.

* * * * *